United States Patent
Kimura et al.

(10) Patent No.: US 9,452,254 B2
(45) Date of Patent: Sep. 27, 2016

(54) METHOD FOR CONTROLLING A BLOOD COMPONENT SEPARATION DEVICE INCLUDING TEMPORARILY STORING A COMPONENT IN A CONTAINER

(71) Applicant: TERUMO KABUSHIKI KAISHA, Tokyo (JP)

(72) Inventors: Shigeyuki Kimura, Shizuoka (JP); Takemi Kobayashi, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/640,084

(22) Filed: Mar. 6, 2015

(65) Prior Publication Data

US 2015/0174313 A1    Jun. 25, 2015

Related U.S. Application Data

(63) Continuation of application No. PCT/JP2012/073199, filed on Sep. 11, 2012.

(51) Int. Cl.
*B04B 11/00* (2006.01)
*A61M 1/36* (2006.01)
*A61M 1/02* (2006.01)

(52) U.S. Cl.
CPC ......... *A61M 1/3696* (2014.02); *A61M 1/0218* (2014.02); *A61M 1/0231* (2014.02); *A61M 1/3693* (2013.01); *A61M 2202/0413* (2013.01);
(Continued)

(58) Field of Classification Search
CPC ........... A61M 1/3696; A61M 1/0231; A61M 1/0218; A61M 1/3693; A61M 2202/0427; A61M 2202/0413; B04B 1/02; B04B 11/00; B04B 11/04; B04B 13/00
USPC ...................................... 494/37, 42
See application file for complete search history.

(56) References Cited

U.S. PATENT DOCUMENTS 6,743,192 B1    6/2004    Sakota et al.
2003/0066807 A1    4/2003    Suzuki

FOREIGN PATENT DOCUMENTS

| JP | 2000084066 A | 3/2000 |
| JP | 2003088581 A | 3/2003 |
| JP | 2003516175 A | 5/2003 |

(Continued)

OTHER PUBLICATIONS

English translation of International Search Report for PCT Application No. PCT/2012/073199, Japanese Patent Office, mail date Dec. 11, 2012, pp. 1-2.

(Continued)

*Primary Examiner* — Charles Cooley
*Assistant Examiner* — Shuyi S Liu
(74) *Attorney, Agent, or Firm* — John R. Merkling

(57) ABSTRACT

The object of the invention is to provide a blood separation device that can reduce the total time for drawing blood to obtain high-concentration platelet liquid, thereby reducing the binding time of the blood donor. The device includes a temporary storage bag (Y2) (also serves as a buffy coat bag) which is a whole blood bag for storing whole blood drawn from a blood donor. The controlling unit of the device controls the device to draw whole blood from the blood donor in parallel with at least either a circulation flow step or an acceleration step, thereby storing the drawn whole blood in the temporary storage bag (Y2).

16 Claims, 20 Drawing Sheets

(52) U.S. Cl.
CPC ....... *A61M 2202/0427* (2013.01); *B04B 11/00* (2013.01)

(56) References Cited

FOREIGN PATENT DOCUMENTS

| JP | 03850429 A | 10/2005 |
|---|---|---|
| JP | 2009226210 A | 10/2009 |
| JP | 2012081213 A | 4/2012 |
| WO | WO0128621 A | 4/2001 |
| WO | WO2008056733 A1 | 5/2008 |

OTHER PUBLICATIONS

English Translation of the International Written Opinion and Preliminary Report on Patentability for PCT Application No. PCT/JP2012/073199, dated Mar. 26, 2015, performed by the International Bureau of WIPO, 12 pages, Geneva Switzerland.

METHOD FOR CONTROLLING A BLOOD COMPONENT SEPARATION DEVICE INCLUDING TEMPORARILY STORING A COMPONENT IN A CONTAINER

TECHNICAL FIELD

The present invention relates to a blood component separation device including a centrifugal separator for separating a predetermined blood component from blood and a container for containing the centrifugally separated predetermined blood component.

BACKGROUND ART

Conventionally, in the field of blood drawing, a blood component such as platelets is collected by collecting only the component from drawn blood and returning the remaining blood components to the blood donor. In such operation, a blood component separation device including a centrifugal separator is used.

In recent years, in the field of radiation therapy of cancer or the like, transfusion of platelet liquid is widely performed, and high-concentration platelet liquid is necessary. To obtain high-concentration platelet liquid, Patent Literature 1 discloses an art using a blood component separation device to temporarily store low-concentration platelet liquid in a buffy coat bag and store only high-concentration platelet liquid in a platelet intermediate bag. Thus, from the centrifugal separator, the low-concentration platelet liquid flows out first, then the high-concentration platelet liquid flows out, and finally the low-concentration platelet liquid flows out. When the low-concentration platelet liquid, which flows out first and last, is stored in the platelet intermediate bag, the concentration of the platelet liquid stored in the platelet intermediate bag inevitably decreases. To prevent the decrease in concentration, the low-concentration platelet liquid that flows out first and last is temporarily stored in the buffy coat bag. Then in the second cycle, the temporarily stored low-concentration platelet liquid is mixed with whole blood drawn from the blood donor and transferred to the centrifugal separator. By repeating this process, only high-concentration platelet liquid is stored in the platelet intermediate bag.

CITATION LIST

Patent Literature

Patent Literature 1: JP 3850429 B1
Patent Literature 2: JP 2009-226210 A

SUMMARY OF INVENTION

Technical Problem

The technique disclosed in Patent Literature 1 however has disadvantage as described below. The disadvantage is that when blood drawing is performed to collect a blood component, three or four cycles of blood drawing are required to collect a predetermined amount of high-concentration platelet liquid because the amount of high-concentration platelet liquid collected in one cycle is as small as a few tenths of millimeters. A blood donor is thus kept bound for a long time to draw blood. This gives stress to a busy blood donor. Another disadvantage is that, although a busy blood donor prefers drawing of a blood component, the blood donor cannot but choose the drawing of whole blood.

The invention is made in view of the aforementioned problem. The object of the present invention is to provide a blood component separation device that, when drawing blood to collect high-concentration platelet liquid, can reduce the total time of collecting whole blood, thereby reducing the binding time of a blood donor.

Solution to Problem

To achieve the object, a blood component separation device according to one aspect of the present invention is configured as described below.

(1) A blood component separation device includes a centrifugal separator for separating a predetermined blood component from blood and a container for containing the centrifugally separated predetermined blood component, and performs (a) centrifugal separation step of introducing the whole blood drawn from a blood donor into the centrifugal separator with a first blood pump and separating the whole blood into a plurality of blood components, (b) circulation flow step of introducing the predetermined first blood component, among centrifugally separated blood components, stored in a first container into the centrifugal separator together with whole blood, (c) circulation/acceleration step of stopping the supply of whole blood to the centrifugal separator after separating a predetermined amount of the first blood component in the circulation flow step, introducing only the first blood component stored in the first container to the centrifugal separator with the second blood pump to circulate the first blood component for a predetermined period of time, and increasing the circulation speed in the centrifugal separator to separate and collect a second blood component. The blood component separation device is characterized in that the whole blood drawn from the blood donor is temporarily stored in a temporary storage container during at least a period in the circulation/acceleration step, and one of tubes coupled to the temporary storage container is coupled to an outlet port of the centrifugal separator and the other tube is coupled between the first container and a second blood pump.

(2) The blood component separation device according to (1) is preferably characterized in that the second blood pump introduces, in the centrifugal separation step in the following cycle, at least either the whole blood or the low-concentration second blood component stored in the temporary storage container in the previous cycle into the centrifugal separator.

In this manner, at least either the whole blood or the low-concentration second blood component stored in the previous cycle can quickly and surely be introduced into the centrifugal separator.

(3) The blood component separation device according to (1) or (2) is preferably characterized in that the other tube is branched to be coupled to an outlet port of a first blood pump, an open/close valve is provided on each of two tubes branched from the other tube, an open/close valve is provided to an outlet port of the second blood pump, and an open/close valve is provided to an outlet port of the first container.

In this configuration, at least either the whole blood or the low-concentration second blood component stored in the temporary storage bag can be introduced into the centrifugal separator by using the second blood pump without any additional blood pump, and thus the device need not be large in size, and the cost can be reduced. Furthermore, compared to a device using a difference in elevation instead of a blood pump, at least either the whole blood or the low-concentration second blood component stored in the temporary storage bag Y2 can be introduced into the centrifugal separator E1 in a short time by using the blood pump.

(4) The blood component separation device according to any one of (1) to (3) preferably performs (d) blood returning step, which is performed after collecting the predetermined amount of the second blood component in the circulation/acceleration step, of returning to the blood donor the blood component that is not collected, and is characterized in that the whole blood stored in the temporary storage container is introduced into the centrifugal separator in the centrifugal separation step of the following cycle together with the whole blood drawn in the following cycle, where the steps (a) to (d) constitute one cycle.

In this configuration, in parallel with the circulation/acceleration step in the first cycle (the present cycle), whole blood can be drawn from the blood donor, so that the time of drawing whole blood in the second cycle (the following cycle) can be reduced, thereby reducing the total time of the process and the binding time of the blood donor.

For example, typical time periods in one cycle are nine minutes for blood drawing and the circulation flow step (critical flow step), 30 to 40 seconds for the circulation step in the circulation/acceleration step, 20 to 30 seconds for the acceleration step in the circulation/acceleration step, and about four minutes for the blood returning. According to the present invention, since blood drawing is performed for about one minute in the first cycle, the blood drawing time in the second cycle can be reduced by one minute to about eight minutes. Similarly, when total of three cycles are performed, the blood drawing time in the third cycle can be reduced by one minute to about eight minutes.

For a blood donor, the amount of blood circulating outside the body increases, though it may not be a problem for 90% of blood donors. The donor may be checked in advance to see if there is a problem to increase the amount of blood circulating outside the body. If there may be a problem, a switching unit can be used so as not to perform the drawing of whole blood in parallel with the circulation/acceleration step in the first cycle (the present cycle), but to perform the drawing of whole blood in the second cycle (the following cycle) after returning blood. It goes without saying that the drawing of whole blood for the following cycle is not performed in the last cycle, because there is no cycle following the last cycle.

(5) The blood component separation device according to any one of (1) to (4) is preferably characterized in that the circulation/acceleration step includes a first collecting step of transferring a portion of the second blood component with low-concentration to a temporary storage container and a second collecting step of collecting a portion of the second blood component with high-concentration, and that the low-concentration second blood component transferred to the temporary storage container and the whole blood collected in the temporary storage container in the following cycle are introduced into the centrifugal separator together with whole blood drawn in the following cycle.

In this configuration, the BC recycling for obtaining high-concentration platelets can be used and, along with the circulation/acceleration step in the first cycle (the present cycle), the whole blood can be drawn from the blood donor, so that the time of drawing whole blood in the second cycle (the following cycle) can be reduced, thereby reducing the total time of the process and the binding time of the blood donor.

(6) The blood component separation device according to (5) preferably includes a second container for temporarily storing the low-concentration second blood component in the circulation/acceleration step, and is characterized in that the second container also serves as the temporary storage container.

In this configuration, an additional second container is not required so that the device need not be made large in size, and since a special disposable second container is not required, the cost can be reduced.

DESCRIPTION OF EMBODIMENTS

Figure 1:
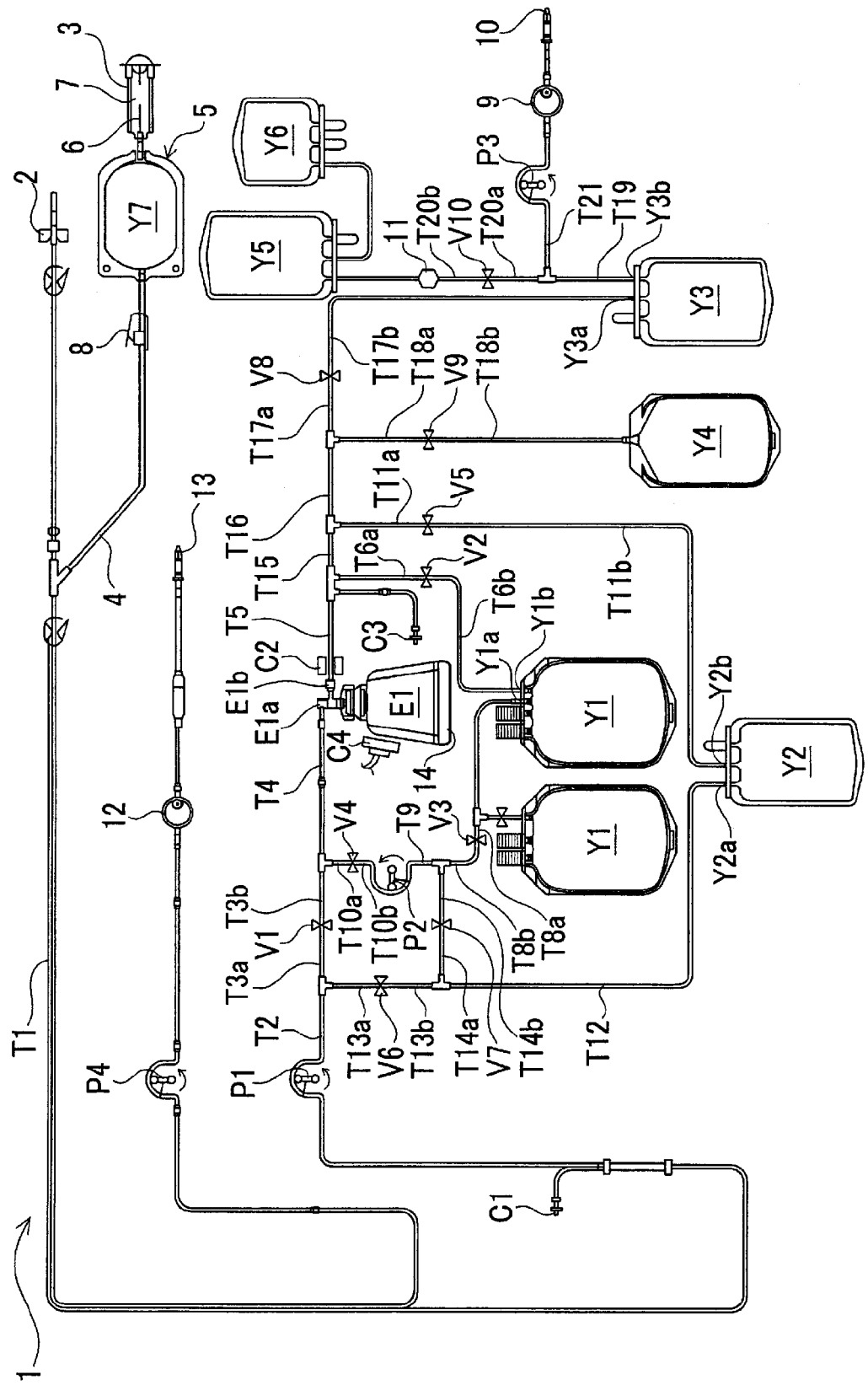
FIG. 1 illustrates a configuration of a blood component separation device according to a first working example of the present invention.
Figure 20:
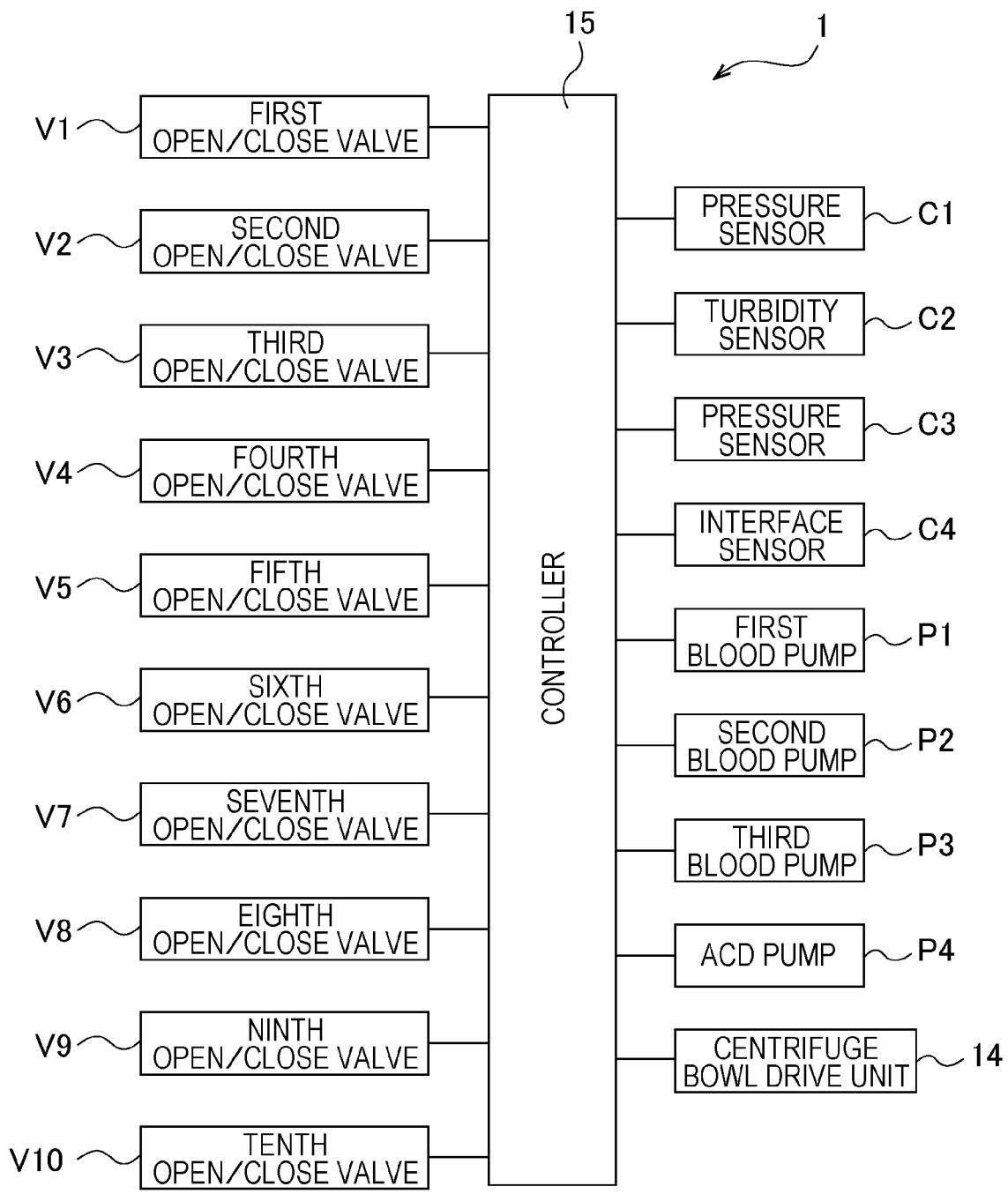
FIG. 20 is a block diagram illustrating a control system of the blood component separation device according to an embodiment.

FIG. 1 illustrates a system configuration of a blood component separation device according to the present invention. FIG. 20 is a block diagram illustrating a control system of the blood component separation device according to an embodiment.

The blood component separation device according to the embodiment includes a blood component separation circuit 1. The blood component separation circuit 1 includes an initial flow blood collecting circuit 5 composed of a blood drawing needle 2, an initial flow blood collecting bag Y7 for collecting initial flow blood, a sampling port 3, and an initial flow blood collecting line 4. The blood component separation circuit 1 includes a centrifuge bowl E1. The centrifuge bowl E1 includes a rotor (not shown) having therein a space for storing drawn blood, a rotor drive unit 14 for rotating the rotor, an inflow port (first port E1a), and an outflow port (second port E1b), and is configured to separate blood into a plurality of blood components by rotating the rotor. The blood component separation circuit 1 includes three containers for storing blood components separated in the centrifuge bowl E1, that is, a first container (plasma bag) Y1, a second container (temporary storage bag) Y2, and a third container (platelet intermediate bag) Y3. The blood component separation circuit 1 includes a first line, a second line, a third line, a fourth line, a fifth line, a sixth line, and a seventh line. The first line couples the blood drawing needle 2 and the centrifuge bowl E1 and includes a donor tube T1, a first blood pump P1, a tube T2, a tube T3a, a first open/close valve V1, a tube T3b, and a tube T4. The second line couples the centrifuge bowl E1 and the first container Y1 and includes a tube T5, a tube T6a, a second open/close valve V2, and a tube T6b. The third line couples the first container Y1 and the first line and includes a tube T8a, a third open/close valve V3, a tube T8b, a tube T9, a second blood pump P2, a tube T10b, a fourth open/close valve V4, and a tube T10a. The fourth line couples the centrifuge bowl E1 and the second container Y2 and includes a tube T5, a tube T15, a tube T11a, a fifth open/close valve V5, and a tube T11b. The fifth line couples the second container Y2 and the first line and includes a tube T12, a tube T13b, a sixth open/close valve V6, and a tube T13a. The sixth line couples the second container Y2 and the first line, similarly to the fifth line, and includes a tube T12, a tube T14a, a seventh open/close valve V7, a tube T14b, a tube T9, the second blood pump P2, the tube T10b, the fourth open/close valve V4, and the tube T10a. The seventh line couples the centrifuge bowl E1 and the third container Y3 and includes the tube T5, the tube T15, a tube T16, a tube T17a, an eighth open/close valve V8, and a tube T17b.

The blood drawing needle 2 for drawing whole blood (blood) from a blood donor is coupled to the first port of the first blood pump P1 via the donor tube T1. The initial flow blood collecting bag Y7 is coupled to the blood drawing needle 2 via a branch provided on the donor tube T1 and via the initial flow blood collecting line 4. The initial flow blood collecting bag Y7 includes a sampling port 3 for transferring collected initial flow blood to a test container (not shown). The sampling port 3 is constituted with a main body, a needle 6, and a cover 7 for covering the needle. Further, a clamp 8 is provided on the initial flow blood collecting line to open/close the line.

The tube T2 coupled to the second port of the first blood pump P1 is branched into the tube T3a and the tube T13a. The tube T3a is coupled to the first port of the first open/close valve V1, and the second port of the first open/close valve V1 is coupled to the tube T3b. The tube T3b is branched into the tube T4 and the tube T10a. The tube T4 is coupled to the first port E1a of the centrifuge bowl E1, which is a centrifugal separator for separating collected blood into a plurality of blood components. The centrifuge bowl E1 is disposed on the rotor drive unit 14 to be rotated.

The blood drawing needle 2 and the first port E1a, which is an inlet port of the centrifuge bowl E1, are coupled via the first line (the donor tube T1, the first blood pump P1, the tube T2, the tube T3a, the first open/close valve V1, the tube T3b, and the tube T4). A pressure sensor C1 is coupled to the donor tube T1.

The tube T5 coupled to the second port E1b of the centrifuge bowl E1 is branched into the tube T15 and the tube T6a. The tube T6a is coupled to the first port of the second open/close valve V2, and the second port of the second open/close valve V2 is coupled to the tube T6b. The tube T6b is coupled to the second port Y1b of the plasma bag (the first container) Y1.

The second port E1b of the centrifuge bowl E1 and the plasma bag Y1 are coupled via the second line (the tube T5, the tube T6a, the second open/close valve V2, and the tube T6b). Two plasma bags Y1 are provided, though only one plasma bag Y1 is illustrated in FIGS. 2 to 14.

A first port Y1a, or the outlet port, of the plasma bag Y1 is coupled to the tube T8a. The tube T8a is coupled to the first port of the third open/close valve V3. The second port of the third open/close valve V3 is coupled to the tube T8b, and the tube T8b is coupled to the tube T9. The tube T9 is coupled to the second port of the second blood pump P2. The first port of the second blood pump P2 is coupled to the tube T10b, and the tube T10b is coupled to the second port of the fourth open/close valve V4. The first port of the fourth open/close valve V4 is coupled to the tube T10a. The tube T10a is coupled to the intermediate position between the tube T3b and the tube T4 constituting the first line. The plasma bag Y1 and the first line are coupled via the third line (the tube T8a, the third open/close valve V3, the tube T8b, the tube T9, the second blood pump P2, the tube T10b, the fourth open/close valve V4, and the tube T10a). The plasma bag Y1 is thus configured to selectively communicate with the inlet port or the outlet port of the centrifuge bowl E1.

The tube T15 branched from the tube T5 branches into the tube T11a and the tube T16. The tube T11a is coupled to the first port of the fifth open/close valve V5, and the second port of the fifth open/close valve V5 is coupled to the tube T11b. The tube T11b is coupled to the second port Y2b of the temporary storage bag Y2 via the tube T11b. That is, the second port E1b of the centrifuge bowl E1 and the temporary storage bag Y2 are coupled via the fourth line (the tube T5, the tube T15, the tube T11a, the fifth open/close valve V5, and the tube T11b).

The first port Y2a of the temporary storage bag Y2 is coupled to the tube T12, and the tube T12 is branched into the tube T13b and the tube T14a. The tube T13b is coupled to the first port of the sixth open/close valve V6, and the second port of the sixth open/close valve V6 is coupled to the tube T13a. The tube T13a is coupled to the intermediate position between the tube T2 and the tube T3a constituting the first line.

The tube T14a branched from the tube T12 is coupled to the first port of the seventh open/close valve V7, and the second port of the seventh open/close valve V7 is coupled to the tube T14b. The tube T14b is coupled to the intermediate position between the tube T9 and the tube T8b, and the tube T9 is coupled to the second port of the second blood pump P2. The first port of the second blood pump P2 is coupled to the tube T10b, and the tube T10b is coupled to the first port of the fourth open/close valve V4. The second port of the fourth open/close valve V4 is coupled to the tube T10a. The tube T10a is coupled to the intermediate position between the tube T3b and the tube T4 constituting the first line.

The temporary storage bag Y2 and the first line are coupled via the fifth line (the tube T12, the tube T13b, the sixth open/close valve V6, and the tube T13a) and the sixth line (the tube T12, the tube T14a, the seventh open/close valve V7, the tube T14b, the tube T9, the second blood pump P2, the tube T10b, the fourth open/close valve V4, and the tube T10a). The temporary storage bag Y2 is coupled so as to selectively communicate with the inlet port or the outlet port of the centrifuge bowl E1.

The tube T16 branched from the tube T15 branches into the tube T17a and the tube T18a. The tube T17a is coupled to the first port of the eighth open/close valve V8, and the second port of the eighth open/close valve V8 is coupled to the tube T17b. The tube T17b is coupled to the first port Y3a, which is the inlet port of the platelet intermediate bag (the third container) Y3.

The tube T18a branched from the tube T16 is coupled to the first port of the ninth open/close valve V9, and the second port of the ninth open/close valve V9 is coupled to the tube T18b. The tube T18b is coupled to the air bag Y4.

The second port E1b of the centrifuge bowl E1 and the platelet intermediate bag Y3 are coupled via the seventh line (the tube T5, the tube T15, the tube T16, the tube T17a, the eighth open/close valve V8, and the tube T17b). The platelet intermediate bag Y3 is thus configured to communicate with the outlet port of the centrifuge bowl E1.

A turbidity sensor C2 for detecting the concentration of platelets and the pressure sensor C3 are attached to the tube T5 coupled to the second port E1b of the centrifuge bowl E1. The turbidity sensor C2 detects the turbidity, caused by platelets, of plasma flowing in the tube T5. In the peripheral region of where the centrifuge bowl E1 is provided, an interface sensor C4 for detecting the location of the interface of a buffy coat layer BC (see FIG. 15) formed in the centrifuge bowl E1 is attached.

The tube T19 extending from the second port Y3b, or the outlet port, of the platelet intermediate bag Y3, is branched into the tube T20a and the tube T21. The tube T20a is coupled to the first port of the tenth open/close valve V10, and the second port of the tenth open/close valve V10 is coupled to the tube T20b. The tube T21 is coupled to the first port of the third blood pump P3, which is the output port.

The second port, or the input port, of the third blood pump P3 is coupled to a platelet reserve liquid bottle via a sterilizing filter 9 and a bottle needle 10. The tube T20b is coupled to the platelet bag Y5 via a white blood cell removal filter 11. The air bag Y6 is coupled to the platelet bag Y5.

An output port of the ACD pump P4 is coupled to the donor tube T1. The input port of the ACD pump P4 is coupled to the output port of the sterilizing filter 12. The input port of the sterilizing filter 12 is coupled to the ACD storing bottle via a bottle needle 13.

As illustrated in FIG. 20, a controller 15 is configured with, for example, a microcomputer. The controller 15 is electrically coupled to the first blood pump P1, the second blood pump P2, the third blood pump P3, the ACD pump P4, the centrifuge bowl drive unit 14, the pressure sensor C1, the turbidity sensor C2, the pressure sensor C3, the interface sensor C4, the first open/close valve V1, the second open/close valve V2, the third open/close valve V3, the fourth open/close valve V4, the fifth open/close valve V5, the sixth open/close valve V6, the seventh open/close valve V7, the eighth open/close valve V8, the ninth open/close valve V9, and the tenth open/close valve V10.

The detection signals from the sensors C1, C2, C3, and C4 are input to the controller 15. Instructed by these detection signals, the controller 15 controls the pumps P1, P2, P3, and P4 to operate or stop, and controls the rotational direction (normal or reverse) and the rotational speed of the pumps. The controller 15 also controls the open/close valves V1, V2, V3, V4, V5, V6, V7, V8, V9, and V10 to open or close, and controls the centrifuge bowl drive unit 14 to operate as required.

As a material of the tubes, for example, thermoplastic elastomers such as polyvinyl chloride, polyethylene, polypropylene, polyester such as PET and PBT, ethylene-vinyl acetate copolymer (EVA), polyurethane, and polyester elastomer may be used. Among these materials, particularly, polyvinyl chloride is preferably used. Polyvinyl chloride not only has sufficient ductility and flexibility but also is easy to handle and suitable to be choked by a clamp or the like.

As a material of the bags, soft polyvinyl chloride including DEHP as a plasticizer or products of polymerization or copolymerization of such olefins or diolefins as polyolefin, ethylene, propylene, butadiene, and isoprene can be used. Typical examples include ethylene-vinyl acetate copolymer (EVA), polymer blends formed between EVA and various thermoplastic elastomers, and arbitrary combinations thereof. Further, PET, PBT, PCGT, or the like can be used. Among these materials, particularly, polyvinyl chloride is preferably used. Such material having high gas permeability is preferable for a container for storing platelets to improve shelf life of platelets. Therefore, polyolefin or DnDp-plasticized polyvinyl chloride may preferably be used for such material or a material formed in a thin sheet may preferably be used.

Figure 15:
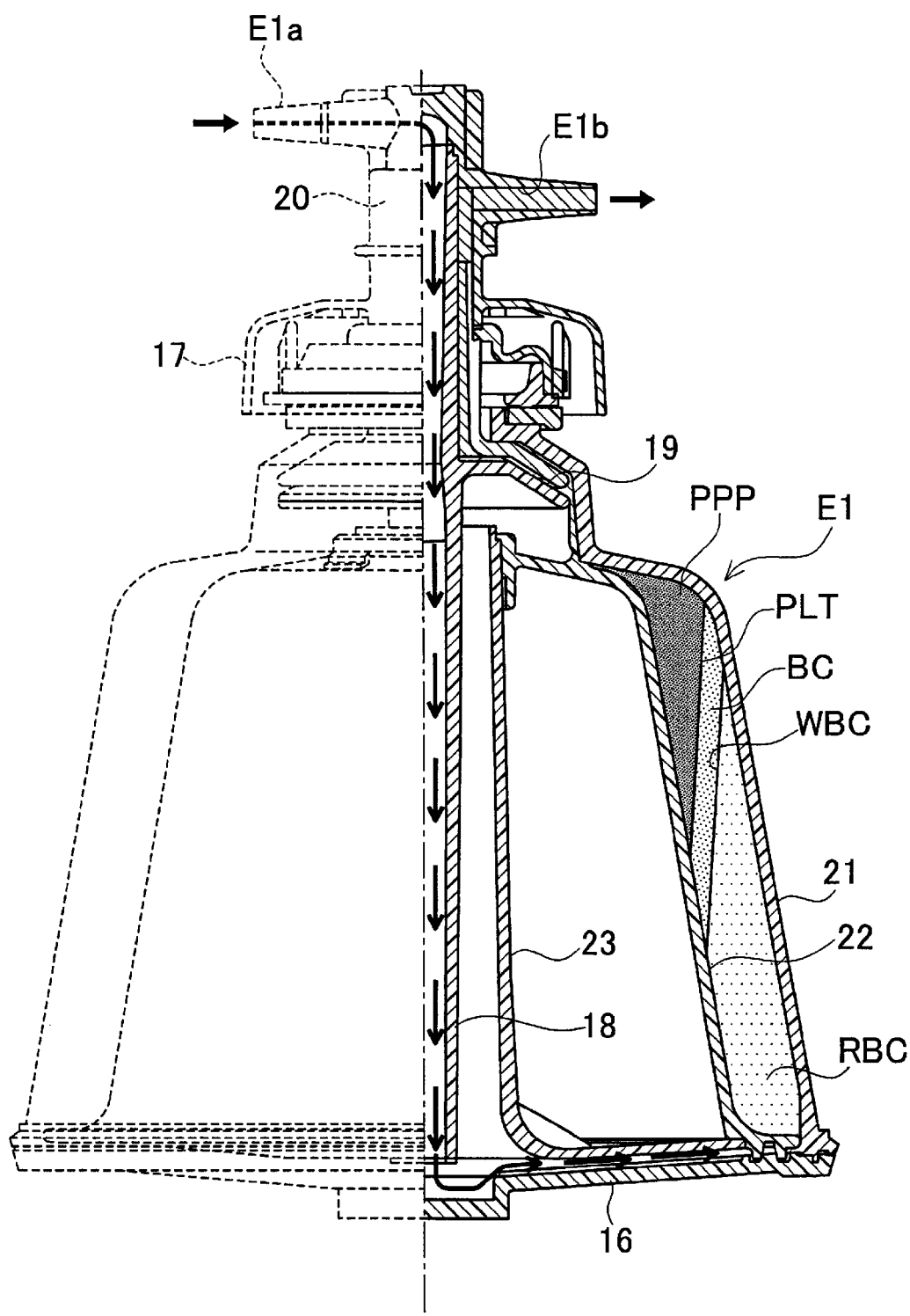
FIG. 15 illustrates a structure of a centrifuge bowl.

FIG. 15 illustrates a structure of the centrifuge bowl E1. In FIG. 15, the figure is divided by the center line, where the right hand side illustrates a sectional view and the left hand side illustrates an external view in dashed lines. The inflow port E1a and the outflow port E1b are formed on the non-rotating fixed portion 20 in the blood component separation device. The fixed portion 20 includes a cover 17 and an inflow tube 18 extending downward. These fixed portions rotatably and integrally support a side wall 21, an outer shell 22, an inner shell 23, and a bottom plate 16. The bottom plate 16 is coupled to the centrifuge bowl drive unit 14 by suctioning so that the rotational force from the centrifuge bowl drive unit 14 can rotate the bottom plate 16. FIG. 15 illustrates a state where whole blood is supplied into the centrifuge bowl E1 from the inflow port E1a and blood components are separated by a centrifugal force.

That is, in the space between the outer shell 22 and the side wall 21 from outer side to inner side, in the descending order of specific gravity, a red blood cell layer RBC, a white blood cell layer WBC, a buffy coat layer BC, a platelet layer PLT, and a plasma layer PPP are formed by a centrifugal force. It is difficult to separate the white blood cell layer WBC and the platelet layer PLT, because the values of their specific gravities are close. Thus, the buffy coat layer BC including the white blood cell layer WBC and the platelet layer PLT exists. Typically, the whole blood includes about 55% of plasma PPP, about 43.2% of red blood cells RBC, about 1.35% of white blood cells WBC, and 0.45% of platelets PLT.

The centrifuge bowl E1 has an outflow passage 19 in the inner periphery formed somewhat above the middle point of the inflow tube 18. So that the plasma layer PPP formed in the inner side of the space formed by the outer shell 22 and the side wall 21 flows out from the centrifuge bowl E1 through the outflow port E1b.

Figure 16:
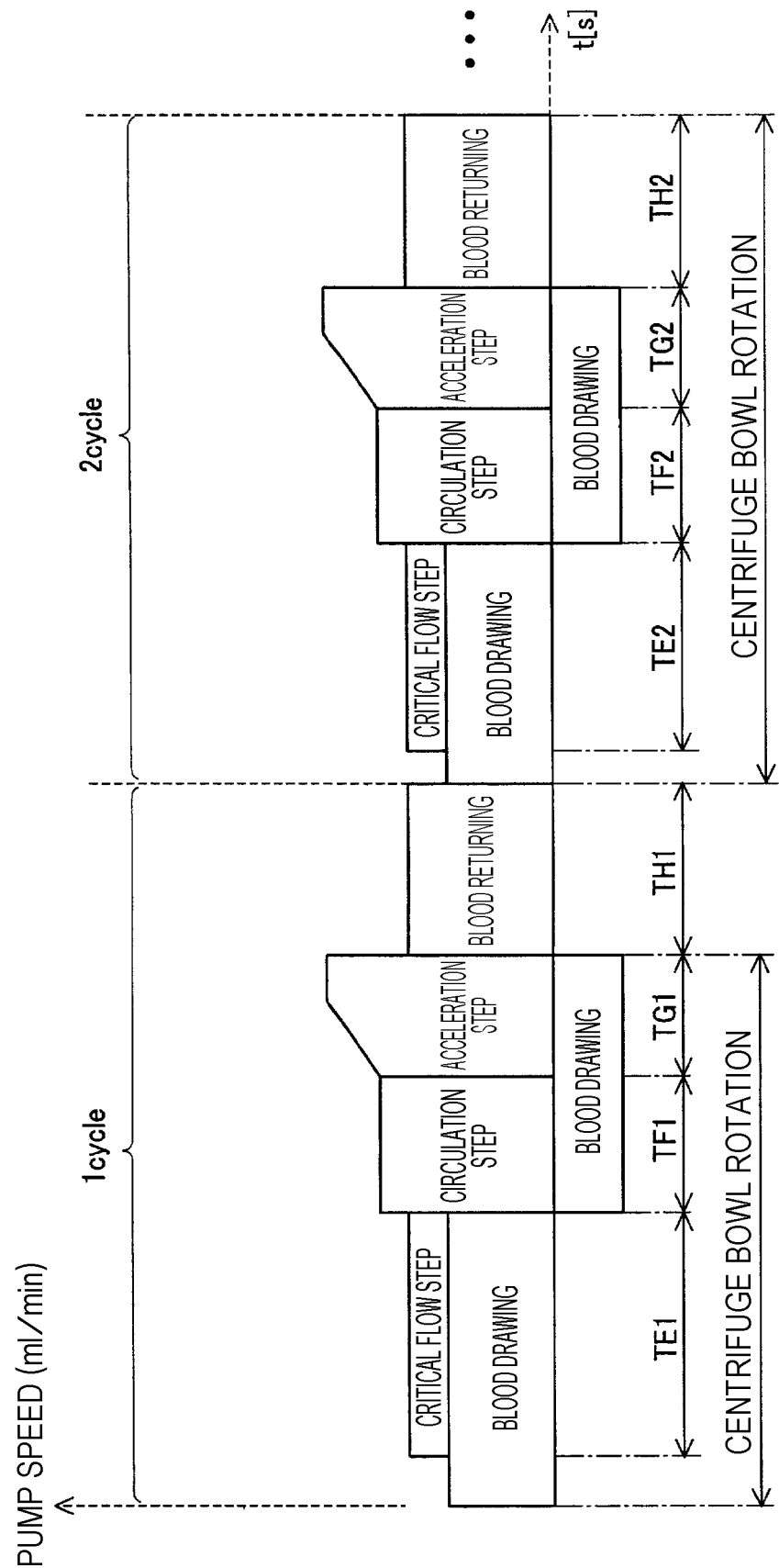
FIG. 16 illustrates an operation of the blood component separation device in a chronological order.

The operation of the blood component separation device configured as described above is illustrated in flow charts in FIGS. 18 and 19. The operation and steps performed in the blood component separation device are illustrated in FIGS. 2 to 14. The object of the device is to collect high-concentration platelet liquid. The pump outlined with a white inside shows that the pump is operating. The pump outlined with a black inside shows that the pump is not operating. The open/close valve outlined with a white inside shows that the valve is opened. The open/close valve outlined with a black inside shows that the valve is closed. FIG. 16 is a processing drawing illustrating the operation of the blood component separation device in a chronological order.

Figure 18:
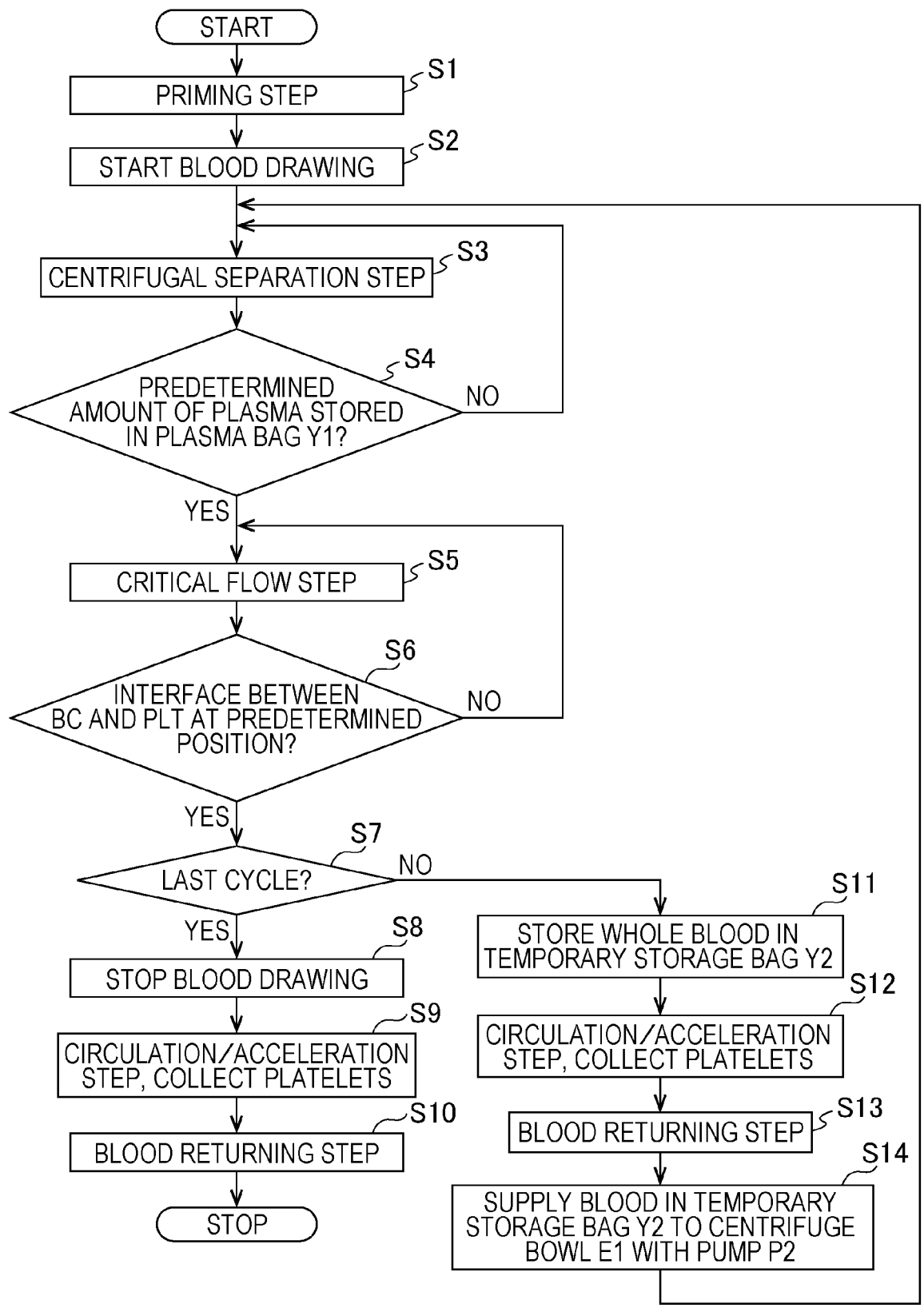
FIG. 18 is a flow chart illustrating an operation of the blood component separation device.

First, a priming step (S1) illustrated in FIG. 18 is performed. The ACD pump P4 and the first pump P1 are operated to supply ACD liquid, which prevents blood coagulation, to the centrifuge bowl E1 through the opened first open/close valve V1, thereby performing the priming step (S1) of the centrifuge bowl E1, the first pump P1, etc. The priming step is performed to previously apply the ACD liquid on portions in the donor tube T1, the first pump P1, the centrifuge bowl E1, etc., which are to make contact with blood, so that the blood will not coagulate when introduced. From the priming step, the centrifuge bowl drive unit 14 rotates the centrifuge bowl E1 at a predetermined rotational speed.

Figure 2:
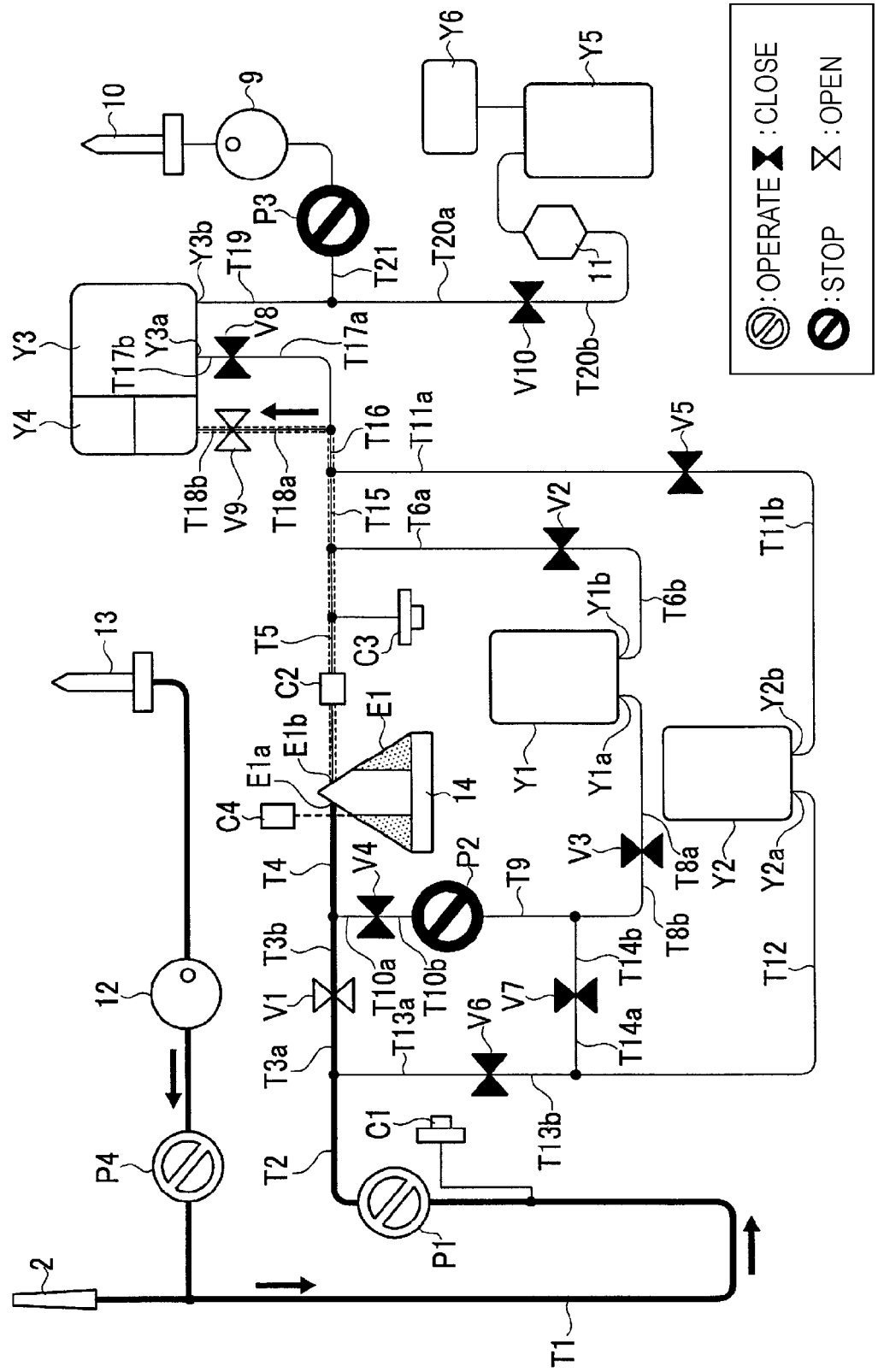
FIG. 2 illustrates a first step (starting blood drawing step) of the blood component separation device according to the first working example of the present invention.

When the priming step (S1) is finished, the blood drawing needle 2 pierces the blood donor to start drawing of whole blood (S2). FIG. 2 illustrates a starting blood drawing step (the first step).

With the blood drawing needle 2 piercing the blood donor, first, the initial flow blood is collected in the initial flow blood collecting bag Y7 in the initial flow blood collecting circuit (see FIG. 1). The branch provided on the donor tube T1 is initially configured to couple the blood drawing needle 2 and the initial flow blood collecting line 4 (see FIG. 1). When a predetermined amount of blood is stored in the initial flow blood collecting bag, the initial flow blood collecting line 4 is choked by the clamp 8 (see FIG. 1) to secure a flow passage toward the first blood pump P1 in the donor tube T1.

The ACD pump P4 is operated again to supply the ACD liquid to the donor tube T1 so that the ACD liquid is mixed with the whole blood, which is then supplied to the centrifuge bowl E1. When whole blood is supplied to the rotating centrifuge bowl E1, the air inside the centrifuge bowl E1 (shown in dashed lines) flows out, pushed by the plasma, through the outflow passage 19 (see FIG. 15) located in the inner periphery of the centrifuge bowl E1, as illustrated in FIG. 2. The air then flows through the opened ninth open/close valve V9 and is stored in the air bag Y4.

In the centrifuge bowl E1, as illustrated in FIG. 15, the supplied whole blood is separated into components by the centrifugal force generated in the bowl.

Figure 3:
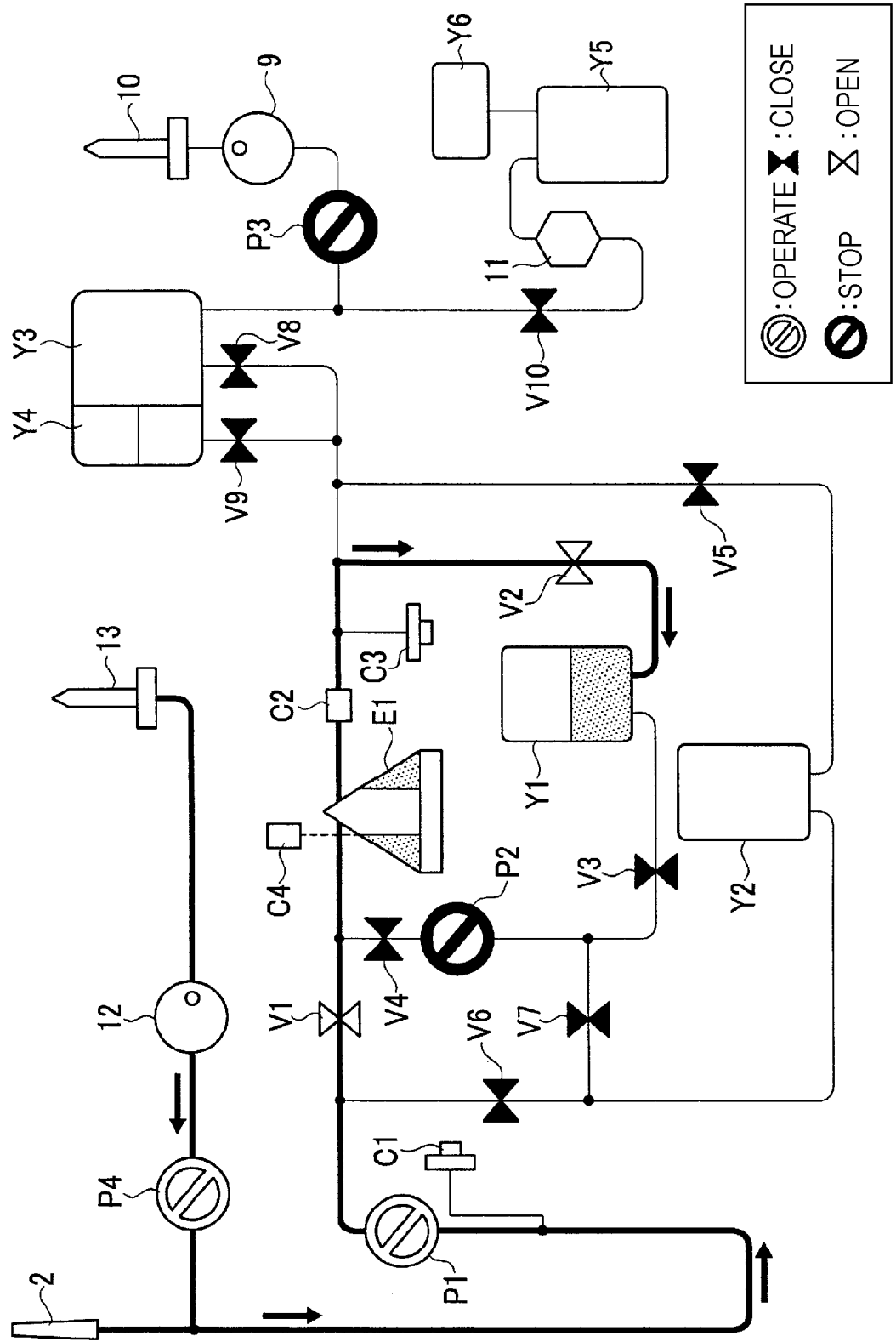
FIG. 3 illustrates a second step (centrifugal separation step).

Then when the turbidity sensor C2 detects that the fluid flowing in the tube has changed from air to plasma, the ninth open/close valve V9 is closed and the second open/close valve V2 is opened to store the plasma spilled out from the centrifuge bowl E1 in the plasma bag Y1, as illustrated in FIG. 3. Thus the centrifugal separation step (S3) is performed. As illustrated in FIG. 15, first, only the plasma comes out from the centrifuge bowl E1.

Figure 4:
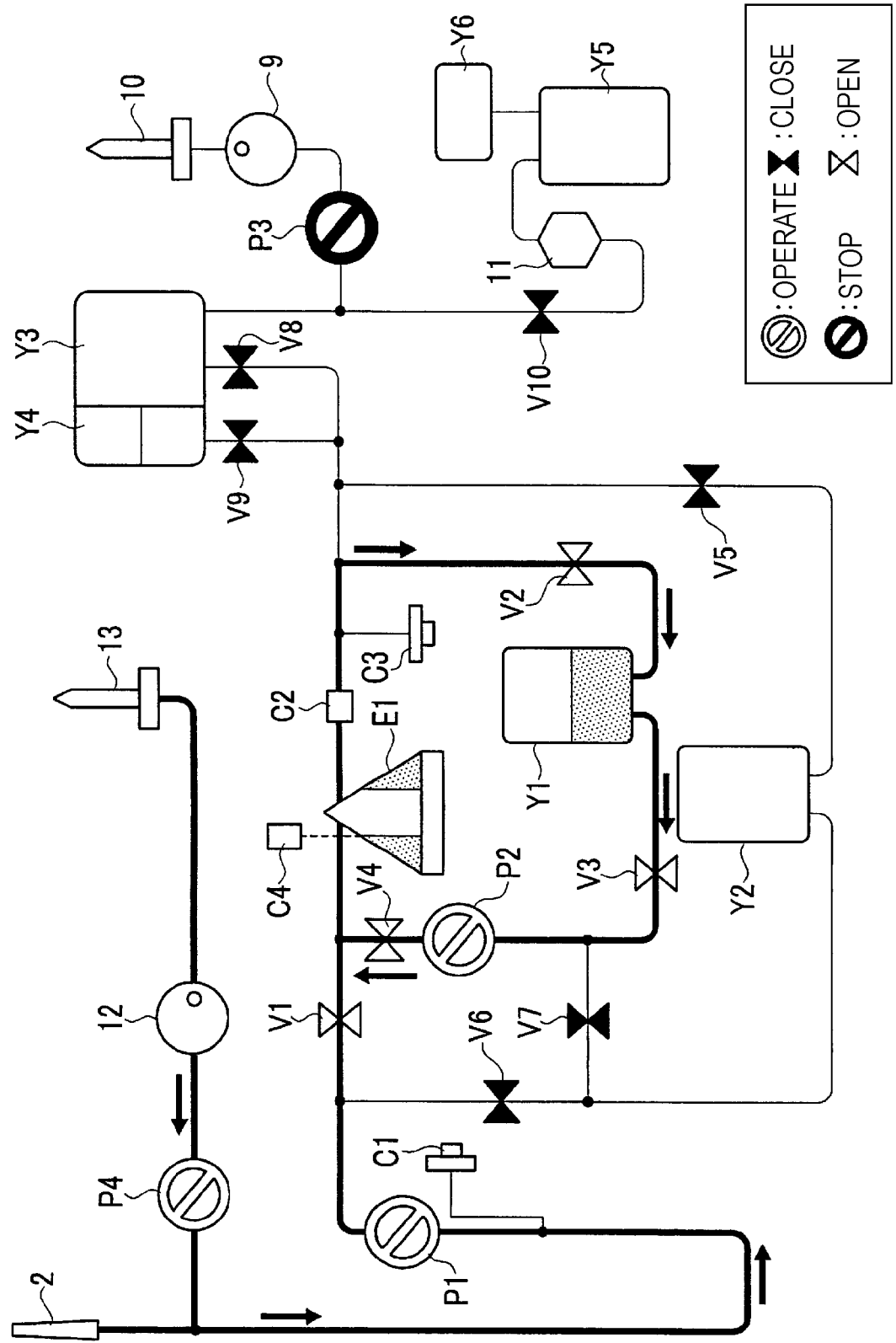
FIG. 4 illustrates a third step (critical flow step).

Then when a certain amount of plasma (30 ml for the working example) is stored in the plasma bag Y1 (S4: YES), the third open/close valve V3 is opened, the second blood pump P2 is operated, and the fourth open/close valve V4 is opened to draw whole blood from the blood donor. Along with this, the whole blood is mixed with the plasma stored in the plasma bag Y1 and supplied to the centrifuge bowl E1, as illustrated in FIG. 4. A third step (critical flow step) S5 is thus performed. These are performed in a critical flow period TE illustrated in FIG. 16.

Figure 5:
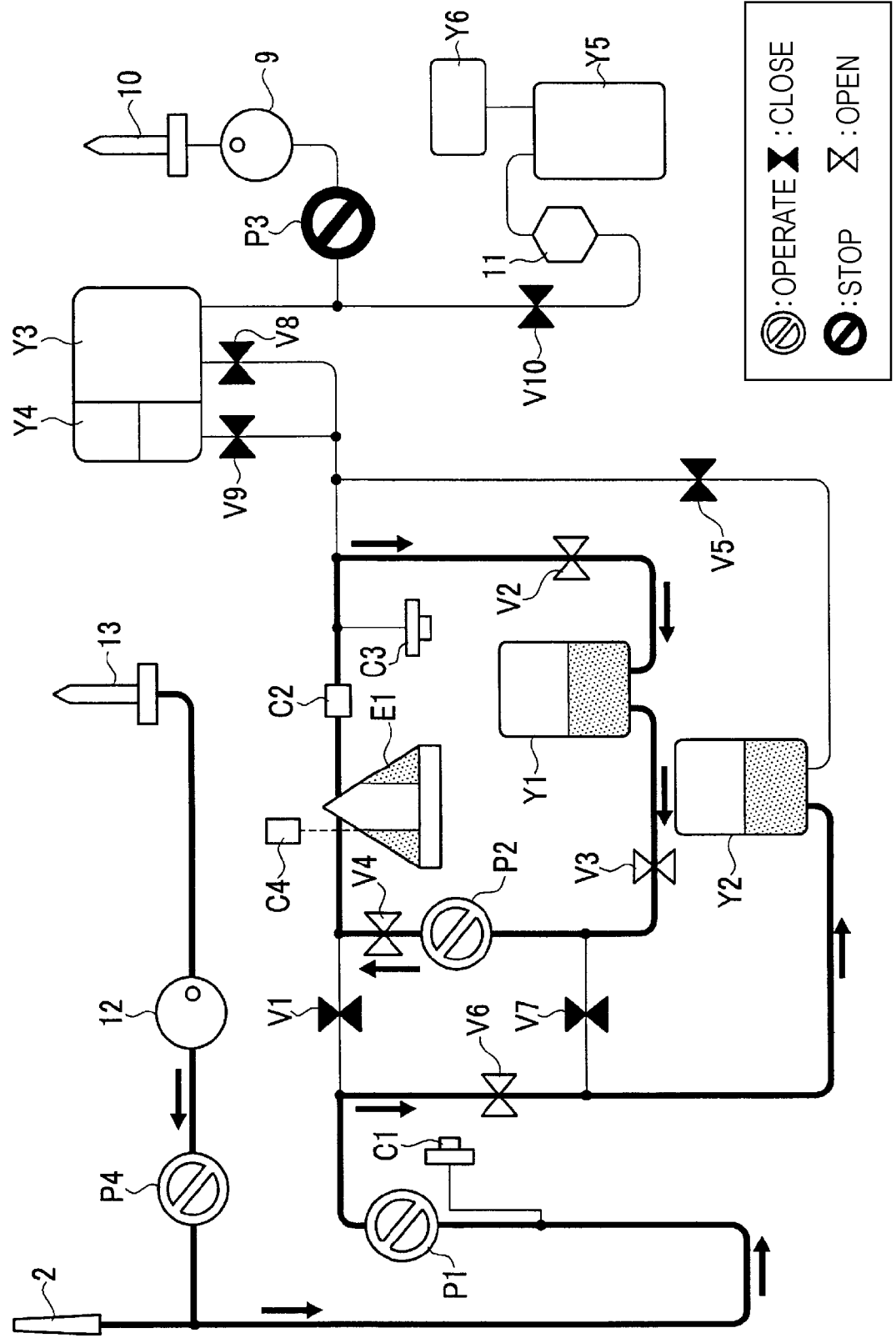
FIG. 5 illustrates a circulation step in a fourth step (circulation/acceleration step).

When the interface sensor C4 detects that the interface between the buffy coat layer BC and the red blood cell layer RBC in FIG. 15 has come to a predetermined position (S6: YES), the second open/close valve V2, the third open/close valve V3, and the fourth open/close valve V4 are kept opened with the second blood pump P2 kept operating as illustrated in FIG. 5. The plasma in the plasma bag Y1 flows through the third open/close valve V3, the second blood pump P2, the fourth open/close valve V4, the centrifuge bowl E1, and the second open/close valve V2 to return to the plasma bag Y1. A circulation step (the fourth step) in the circulation/acceleration step is thus performed (S9, S12). The first open/close valve V1 is closed to prevent the drawn whole blood from flowing into the centrifuge bowl E1. These are performed in a circulation period TF illustrated in FIG. 16.

At the same time, whether the present cycle is the last cycle is determined. When the present cycle is not the last cycle (S7: NO), the sixth open/close valve V6 is opened, with the first blood pump P1 kept operating, to store the drawn whole blood in the temporary storage bag Y2 (S11). In other words, the drawn whole blood is stored in the temporary storage bag Y2 so that the drawing of whole blood can be continued. Drawing of whole blood is continued until the circulation/acceleration step finishes, a predetermined time has elapsed, or a predetermined amount has been drawn. In the last cycle (S7: YES), the first blood pump P1 stops operating to stop blood drawing (S8).

In the circulation step in the circulation/acceleration step of the working example, the circulation speed is set higher than that of the critical flow step so as that the plasma circulates at a speed of about 100 ml/min, thereby flowing through the centrifuge bowl E1 within 30 to 40 seconds. In this manner, the concentration of particulates in the buffy coat layer BC in FIG. 15 decreases, whereby the white blood cell layer WBC having a larger specific gravity than platelets sediments in the outer side of the buffy coat layer BC. That is, the platelet layer PLT and the white blood cell layer WBC can further distinctly be separated.

Figure 6:
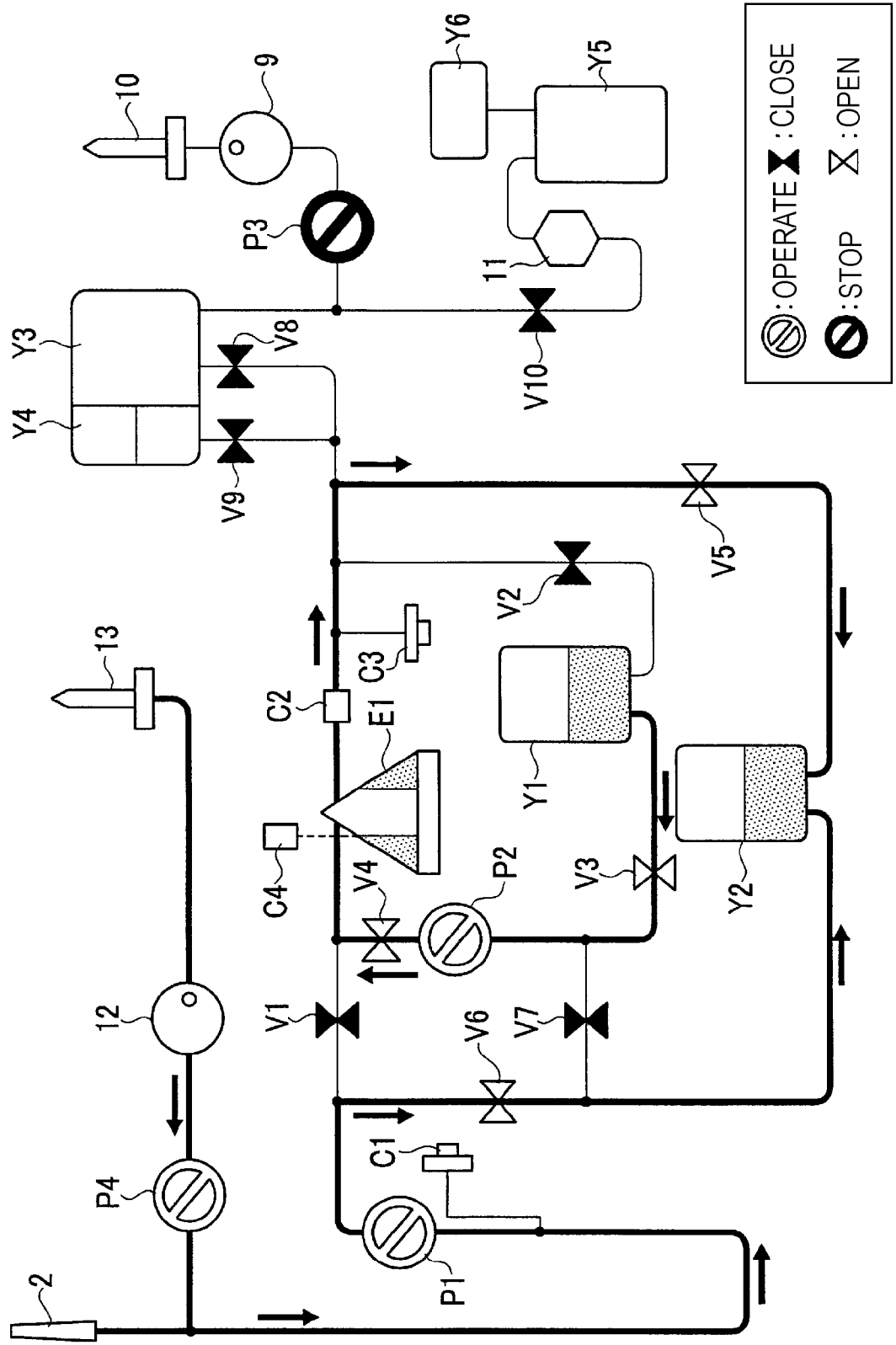
FIG. 6 illustrates a step of collecting low-concentration platelet liquid performed in the fifth step (circulation/acceleration step).

Then after the circulation step performed for a certain period of time, an acceleration step (the fifth step) in the circulation/acceleration step illustrated in FIG. 6 starts. In the acceleration step, the rotational speed of the second blood pump P2 is controlled to gradually increase, thereby gradually increasing the flow rate of plasmas. In the working example, the flow rate of plasma is raised from an initial flow rate of 100 ml/min until platelets flows out. This is performed in an acceleration period TG illustrated in FIG. 16. FIG. 18 illustrates the circulation/acceleration step (S9) representing the circulation step and the acceleration step.

In the acceleration step, the platelets PLT are forced upward and thereby flow out of the centrifuge bowl E1 through the outflow passage 19, as illustrated in FIG. 15. During this acceleration, the white blood cell layer WBC and the red blood cell layer RBC having large specific gravities, therefore receiving greater effect of centrifugal force, will not flow out from the outflow passage 19.

Figure 17:
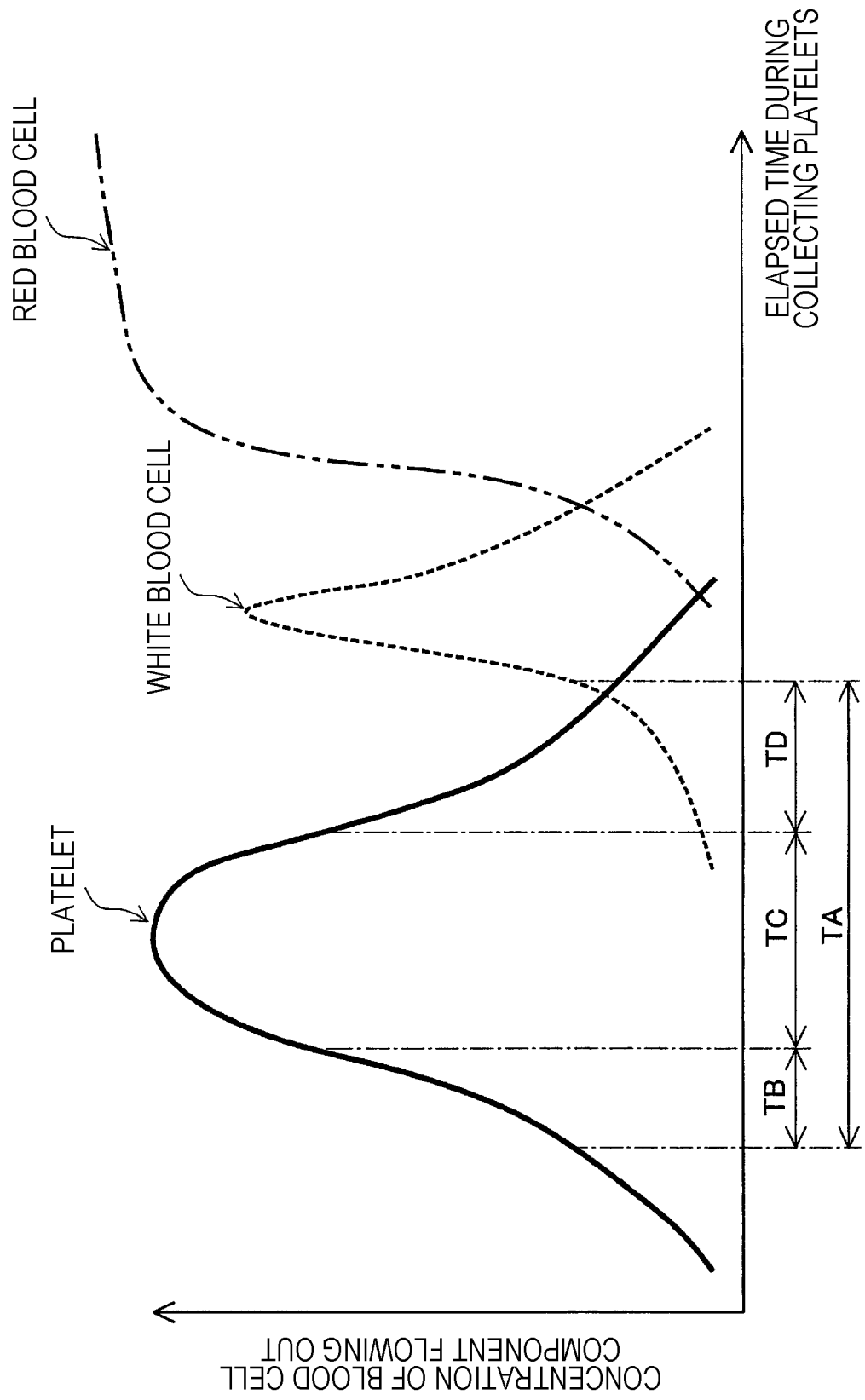
FIG. 17 illustrates changes in concentrations of platelets, white blood cells, and red blood cells flowing out.

FIG. 17 illustrates changes in concentrations of platelets, white blood cells, and red blood cells flowing out. The horizontal axis represents elapsed time during collecting platelets, and the vertical axis represents concentrations of blood cell components flowing out. First, platelets flow out (outflow period TA). In this period, the outflow rate of platelets gradually increases and, after peaking at the maximum flow rate, gradually decreases. Similarly, the outflow rate of white blood cells gradually increases and, after peaking at the maximum flow rate, gradually decreases.

Figure 19:
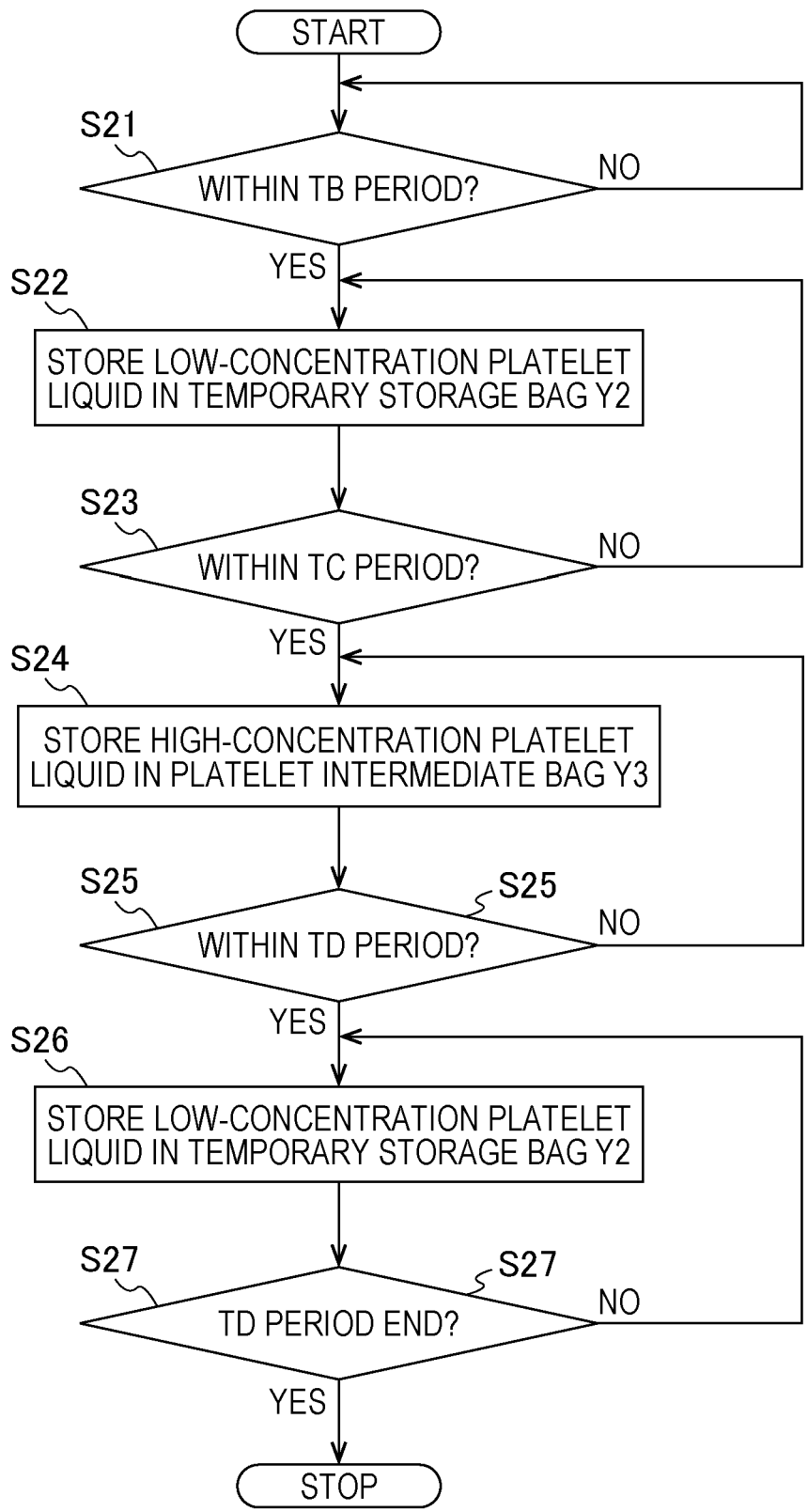
FIG. 19 is a flow chart illustrating an operation performed in a collecting step of collecting platelet liquid.

FIG. 19 illustrates S9 in detail with a flowchart showing the operation of the blood component separation device. The outflow period TA of platelets can be divided into three periods, that is, a low-concentration period TB, which comes first, where low-concentration platelet liquid flows out, a high-concentration period TC, following the TB period, where high-concentration platelet liquid flows out, and a low-concentration period TD, following the TC period, where low-concentration platelet liquid flows out again. Low-concentration platelet liquid is not necessary for obtaining high-concentration platelet liquid.

In the working example, in the acceleration step as illustrated in FIG. 6, when the turbidity sensor C2 detects platelets, that is, when it is determined that the present period is the TB period (S21: YES), the second open/close valve V2 is closed and the fifth open/close valve V5 is opened to store platelet liquid flowing out during the low-concentration period TB in FIG. 17 in the temporary storage bag Y2 (S22). Since the whole blood also flows into the temporary storage bag Y2 to be stored, the low-concentration platelet liquid is stored in the temporary storage bag Y2 mixed with the whole blood. Since the first blood pump P1 is kept operating, the whole blood drawn from the blood donor is continuously stored in the temporary storage bag Y2. Note that, the temporary storage bag Y2 serves as a buffy coat bag as well as a whole blood bag.

Figure 7:
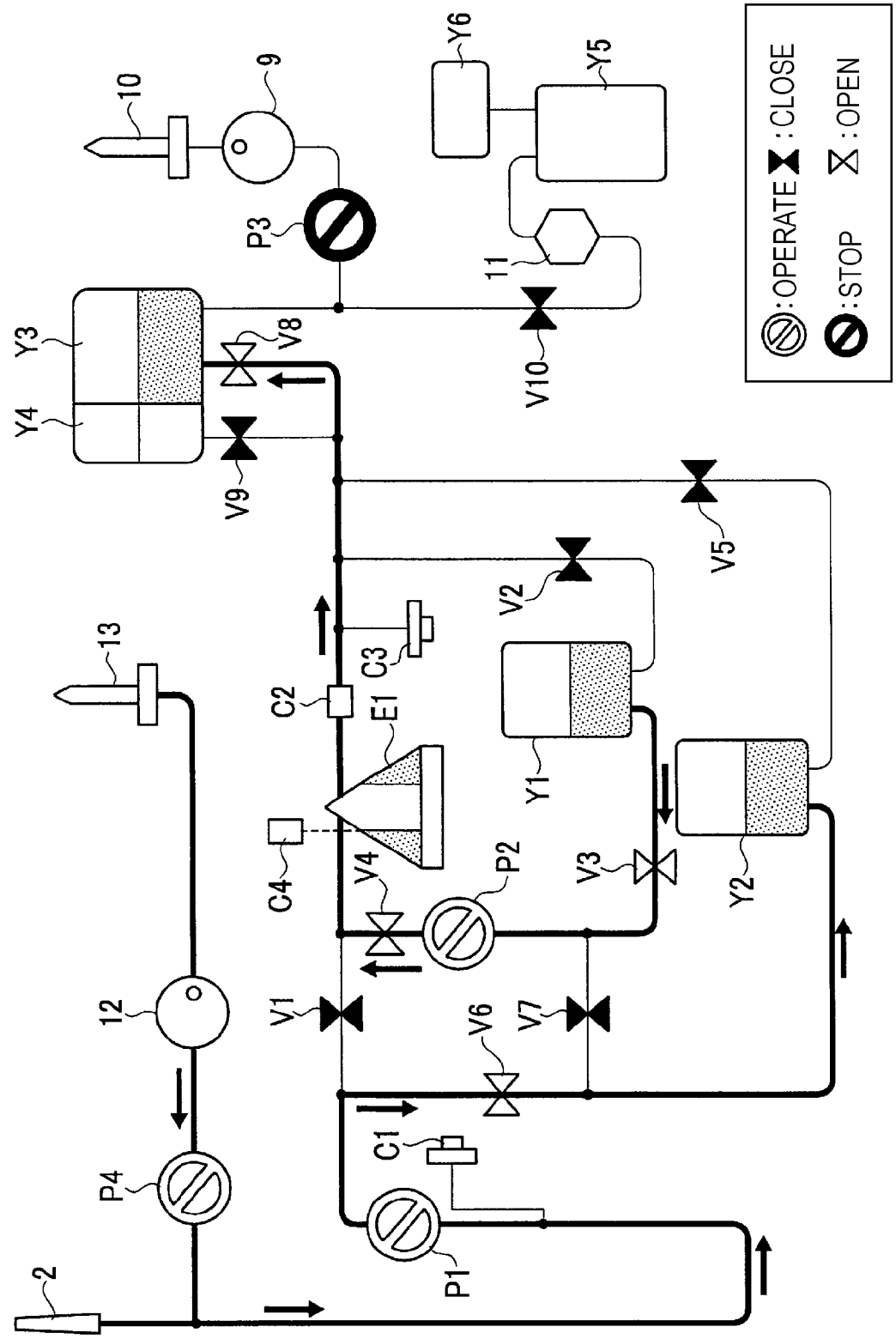
FIG. 7 illustrates a step of storing high-concentration platelet liquid performed in the fifth step (circulation/acceleration step).

When the turbidity sensor C2 detects that the concentration of platelet liquid is high, it is determined that the present period is the TC period (S23: YES), and the fifth open/close valve V5 is closed and the eighth open/close valve V8 is opened as illustrated in FIG. 7. In this manner, the high-concentration platelet liquid flowing out during the high-concentration period TC can be stored in the platelet intermediate bag Y3 (S24).

If the present cycle is not the last cycle (S7: NO), the first blood pump P1 is kept operating so that the whole blood drawn from the blood donor continuously flows through the sixth open/close valve V6 and is stored in the temporary storage bag Y2.

Figure 8:
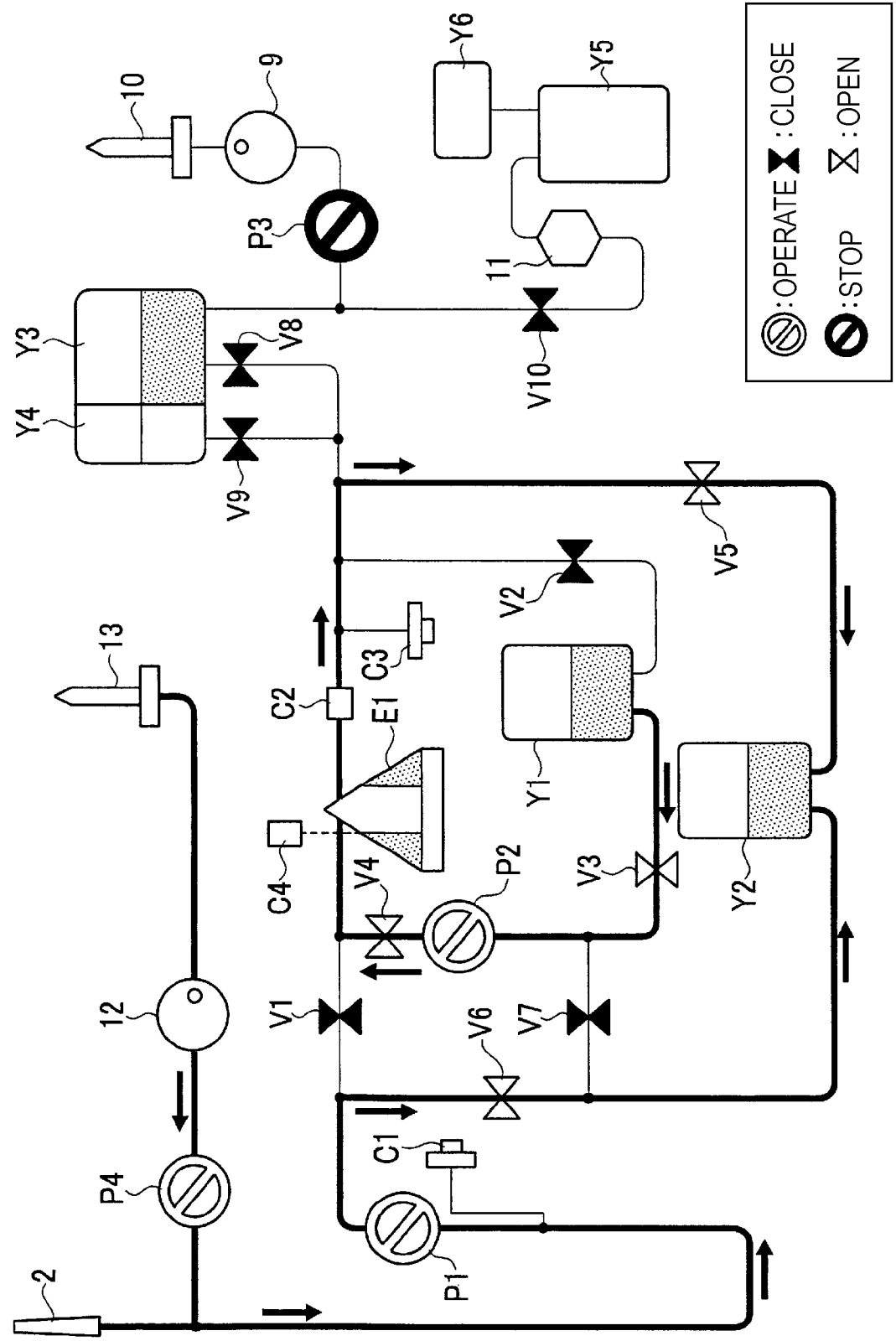
FIG. 8 illustrates a step of collecting low-concentration platelet liquid performed in the fifth step (circulation/acceleration step).
Figure 9:
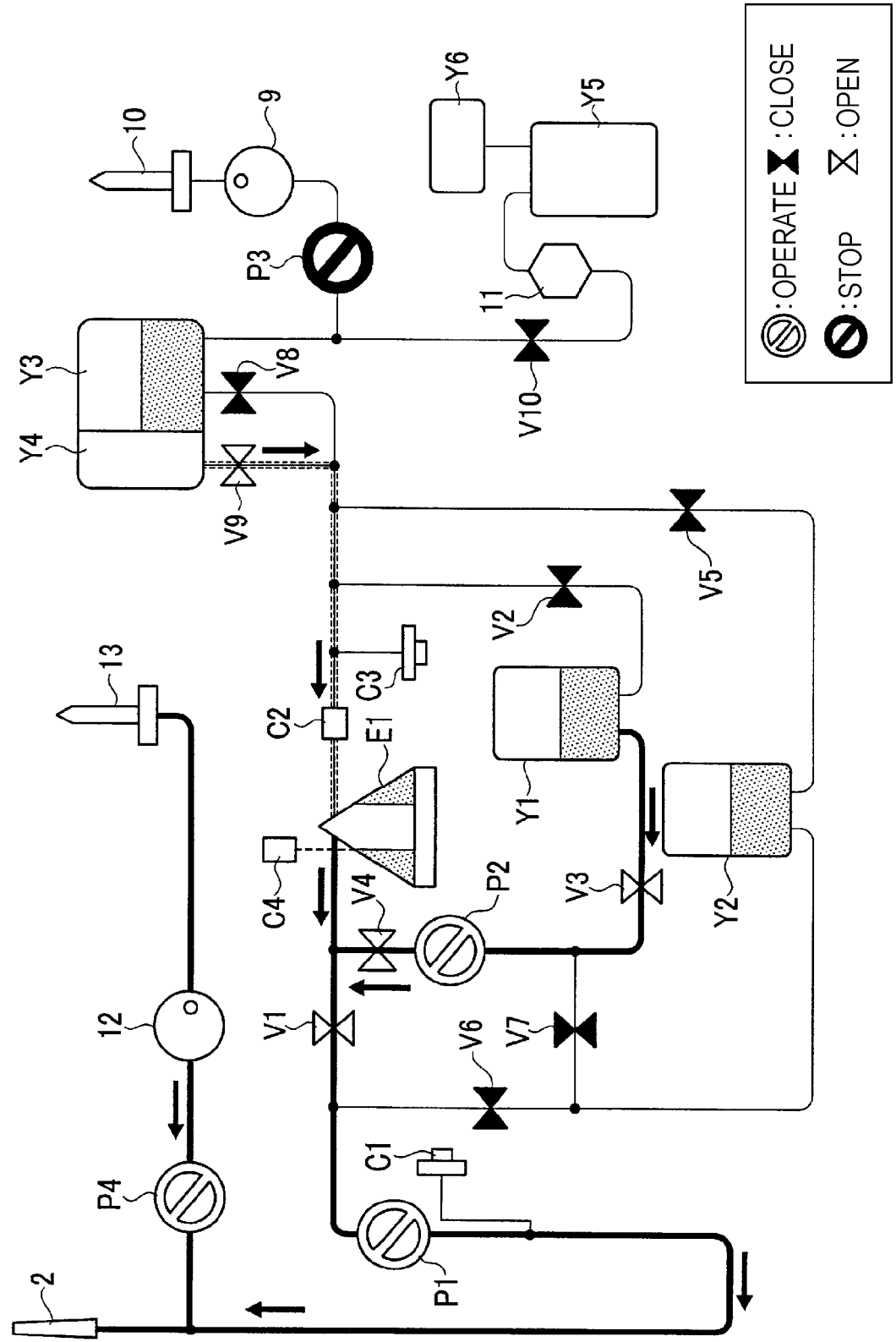
FIG. 9 illustrates a blood returning step.

When the turbidity sensor C2 detects that the turbidity of platelets is below a predetermined value, it is determined that the present period is the TD period (S25: YES), and the eighth open/close valve V8 is closed to block the low-concentration platelet liquid from flowing into the platelet intermediate bag Y3 and the fifth open/close valve V5 is opened, as illustrated in FIG. 8. In this manner, the low-concentration platelet liquid flowing out during the low-concentration period TD can be stored again in the temporary storage bag Y2 (S26).

If the present cycle is not the last cycle (S7: NO), the first blood pump P1 is kept operating so that the whole blood drawn from the blood donor continuously flows through the sixth open/close valve V6 and is stored in the temporary storage bag Y2.

Then when the turbidity sensor C2 detects that the turbidity of platelets is below a predetermined value, it is determined that the TD period is finished (S27: YES), or the outflow of platelets is finished, and the step proceeds to the blood returning step illustrated in FIG. 9 (S10, S13).

In the blood returning step, the centrifuge bowl E1 stops rotation, the sixth open/close valve V6 and the fifth open/close valve V5 are closed, the first open/close valve V1 and the ninth open/close valve V9 are opened, and the first blood pump P1 is reversely rotated, whereby the returning of the blood remaining in the centrifuge bowl E1 to the blood donor starts. The first blood pump P1 is reversely operated at double the rotational speed of the normal rotation to shorten the time of blood returning. Further, as required, the second blood pump P2 is operated to return the excessive plasma stored in the plasma bag Y1.

Figure 10:
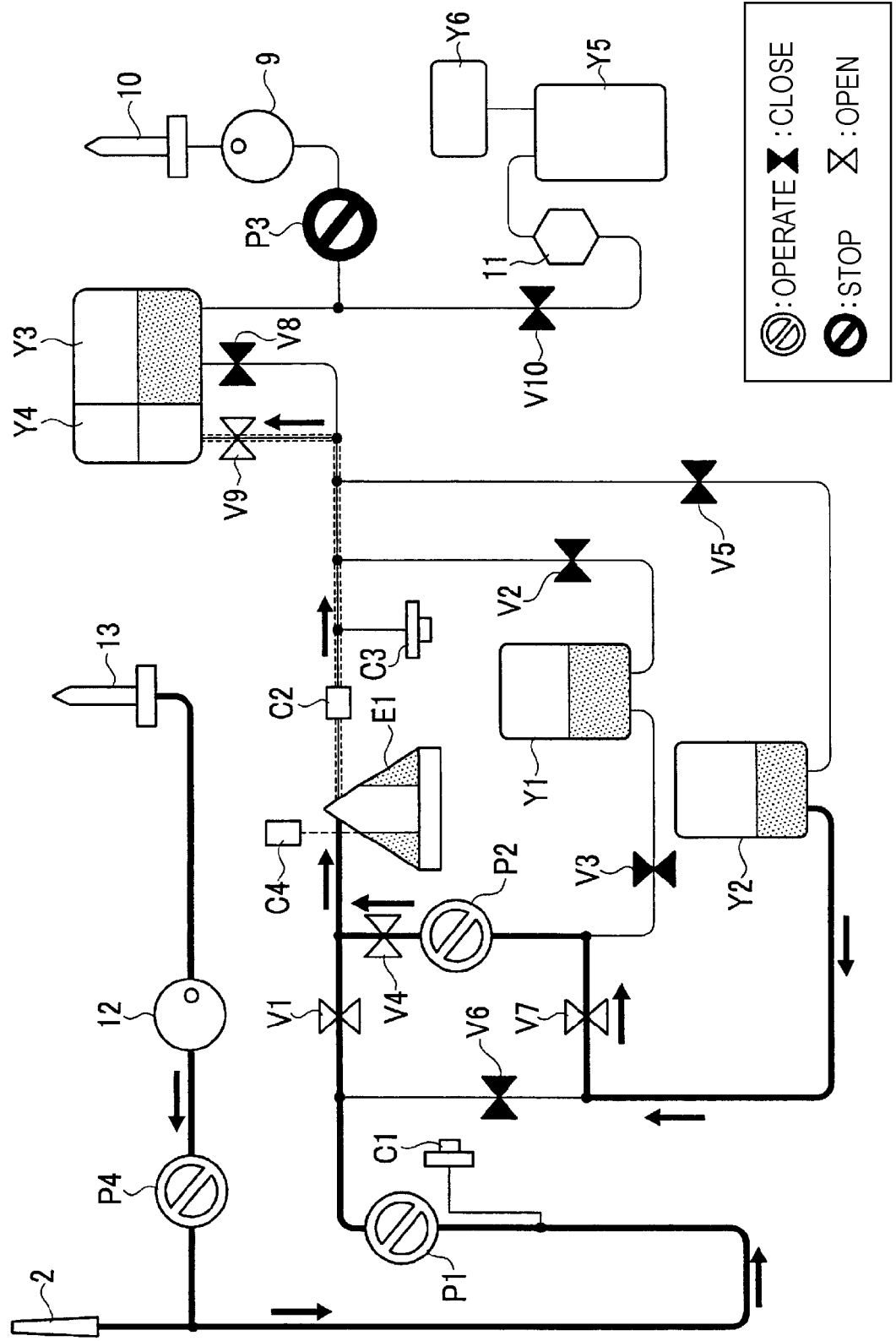
FIG. 10 illustrates the first step performed in a second cycle.

When the blood returning finishes, and if the present cycle is the last cycle (S7: YES), the entire process is finished. When the finished cycle is not the last cycle (S7: NO), the centrifuge bowl E1 starts rotating as illustrated in FIG. 10, and the first blood pump P1 starts normal rotation again to perform blood drawing. The air inside the centrifuge bowl E1 (shown in dashed lines) flows out, pushed by the plasma, through the outflow passage 19 located in the inner periphery of the centrifuge bowl E1. The air then flows through the opened ninth open/close valve V9 and is stored in the air bag Y4. The seventh open/close valve V7 is opened and the second blood pump P2 is operated to allow the blood stored in the temporary storage bag Y2 to flow through the fourth open/close valve V4 into the centrifuge bowl E1 together with the drawn whole blood (S14). The third open/close valve V3 is closed to block the fluid from flowing into the plasma bag Y1.

Figure 11:
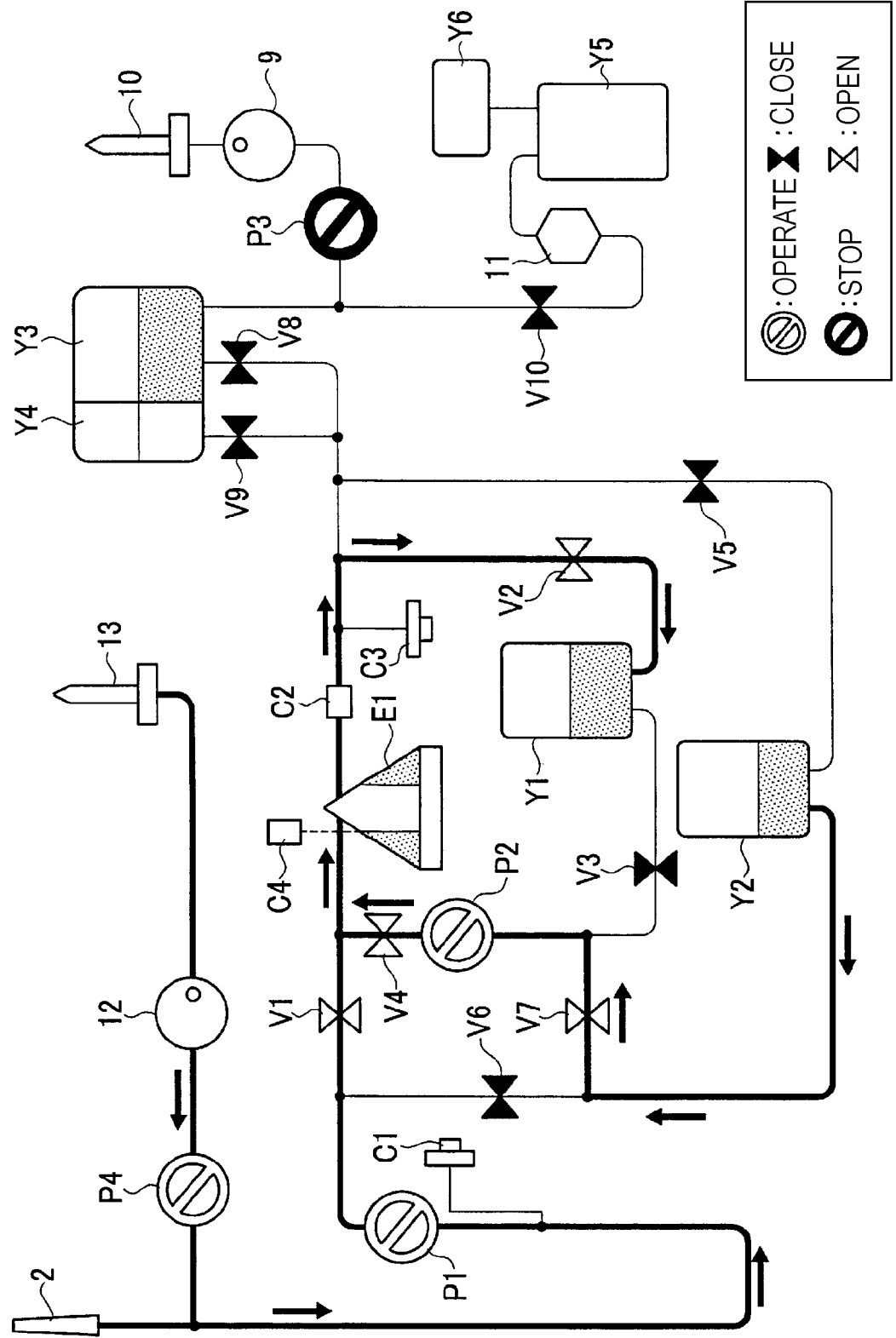
FIG. 11 illustrates the second step performed in the second cycle.

Then when the turbidity sensor C2 detects that the fluid flowing in the tube has changed from air to plasma, the ninth open/close valve V9 is closed and the second open/close valve V2 is opened to store the plasma spilled out from the centrifuge bowl E1 in the plasma bag Y1, as illustrated in FIG. 11.

Figure 12:
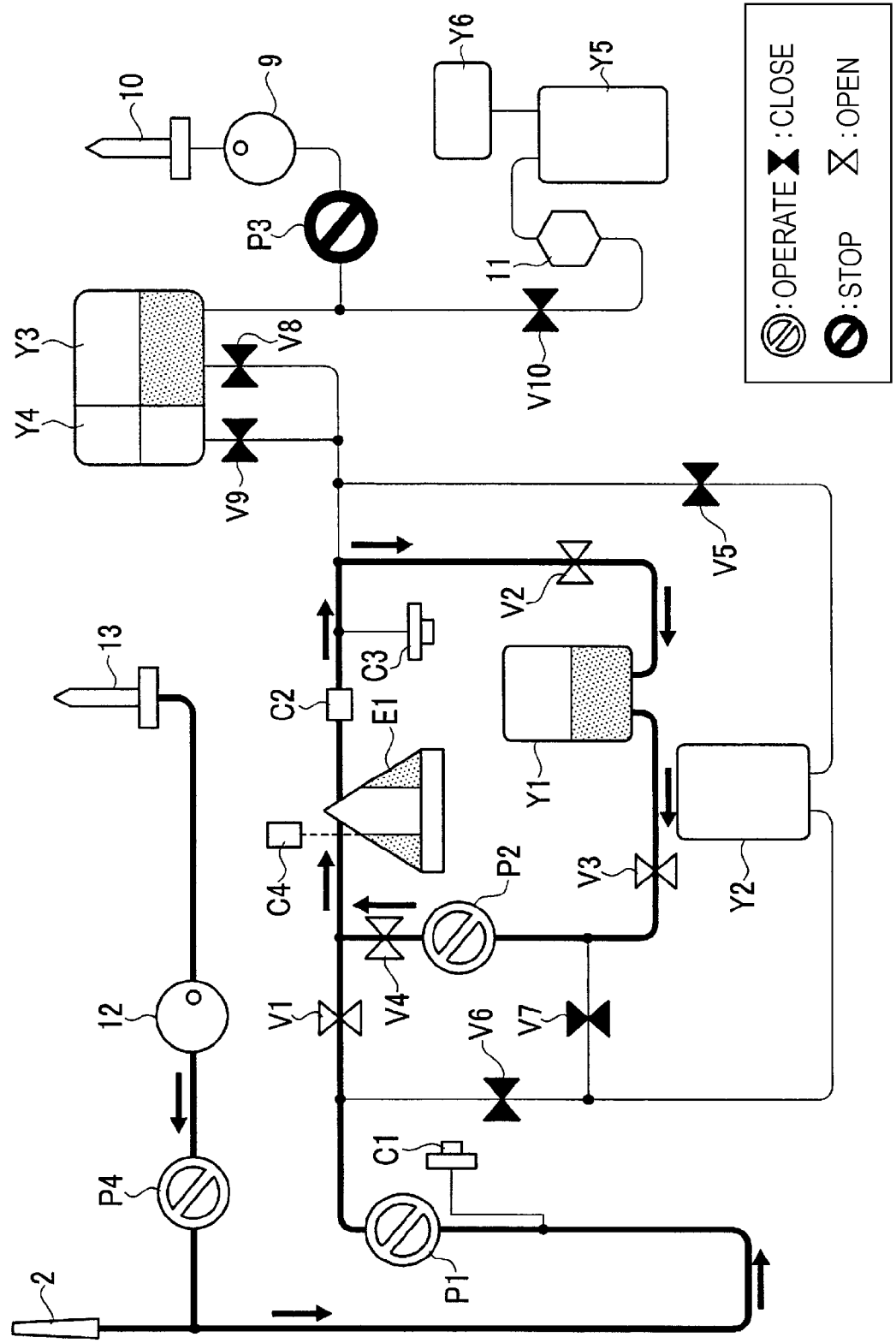
FIG. 12 illustrates the third step performed in the second cycle.

Then when it is confirmed that the whole blood in the temporary storage bag Y2 has returned to the centrifuge bowl E1 and that a predetermined amount of plasma is stored in the plasma bag Y1 (S4: YES), the seventh open/close valve V7 is closed with the second blood pump P2 kept operating, and the third open/close valve V3 is opened to mix the plasma stored in the plasma bag Y1 with the whole blood and to supply the mixture of the plasma and the whole blood to the centrifuge bowl E1, whereby the critical flow step of plasma starts as illustrated in FIG. 12 (the same state as in FIG. 4). The step proceeds to the step illustrated in FIG. 5 (circulation step).

This cycle is repeated, typically three or four times, until a predetermined amount of platelets PLT is obtained. When the operation finishes with three cycles, for example, blood drawing is performed in parallel in a circulation period TF2 and an acceleration period TG2 in the second cycle to store whole blood in the temporary storage bag Y2. Then during blood drawing in the third cycle, the blood in the temporary storage bag Y2 is mixed with whole blood and supplied to the centrifuge bowl E1. Further, in a circulation period TF3 and an acceleration period TG3 in the third cycle, blood drawing is not performed. This is because there is no fourth cycle.

When the operation is to finish with three cycles, blood drawing finishes when the blood drawing needle 2 is removed from the blood donor after completion of the blood returning in the third cycle.

Figure 13:
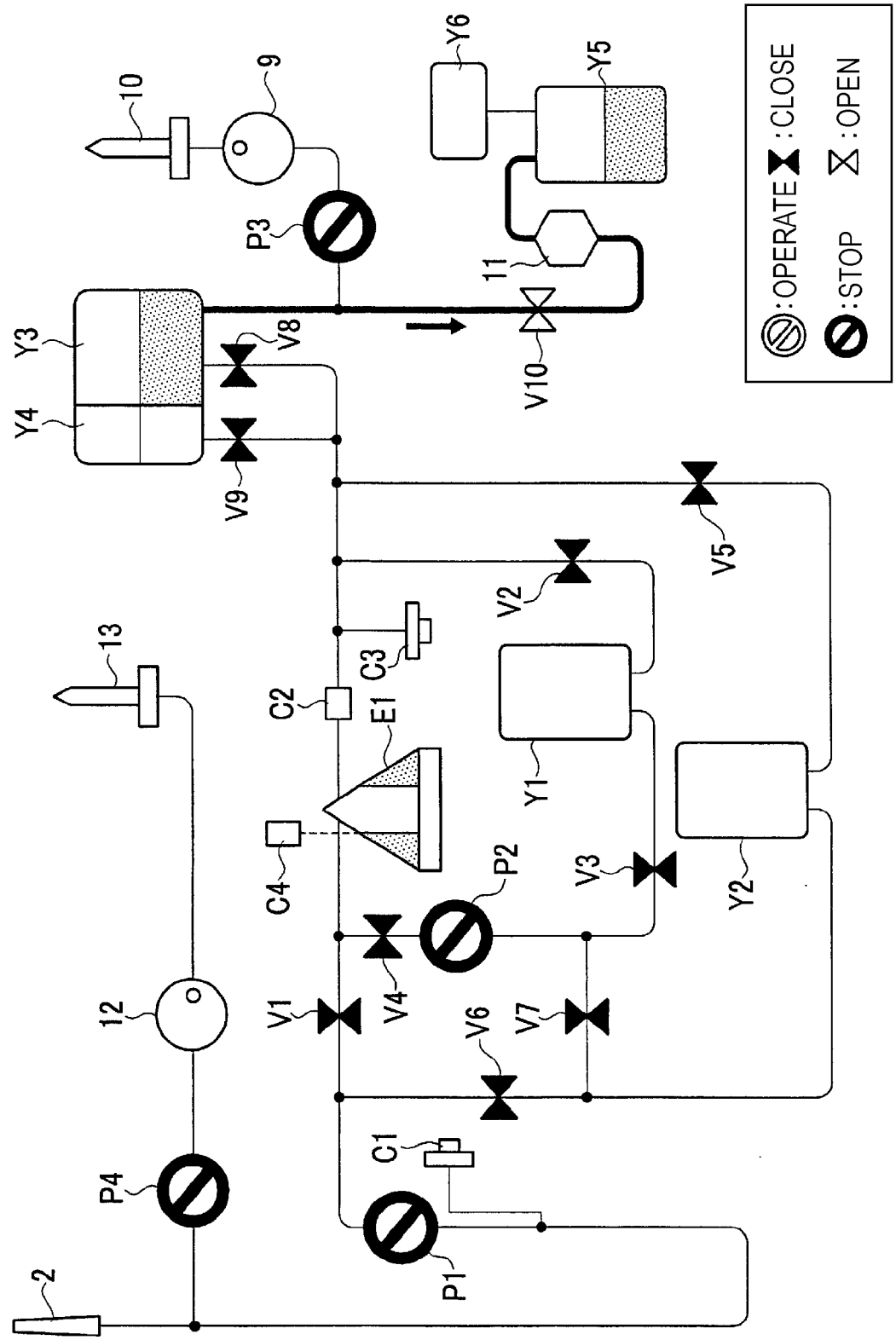
FIG. 13 illustrates a processing step of platelet liquid.

Then, the third blood pump P3 is operated to inject a suitable amount of platelet reserve liquid into the platelet intermediate bag Y3 from a bottle needle 10 coupled to the platelet reserve liquid bottle. As illustrated in FIG. 13, the tenth open/close valve V10 is then opened to inject the high-concentration platelet liquid stored in the platelet intermediate bag Y3 into the platelet bag Y5 through the white blood cell removal filter 11. In this process, the air in the platelet bag Y5 flows into the air bag Y6.

Figure 14:
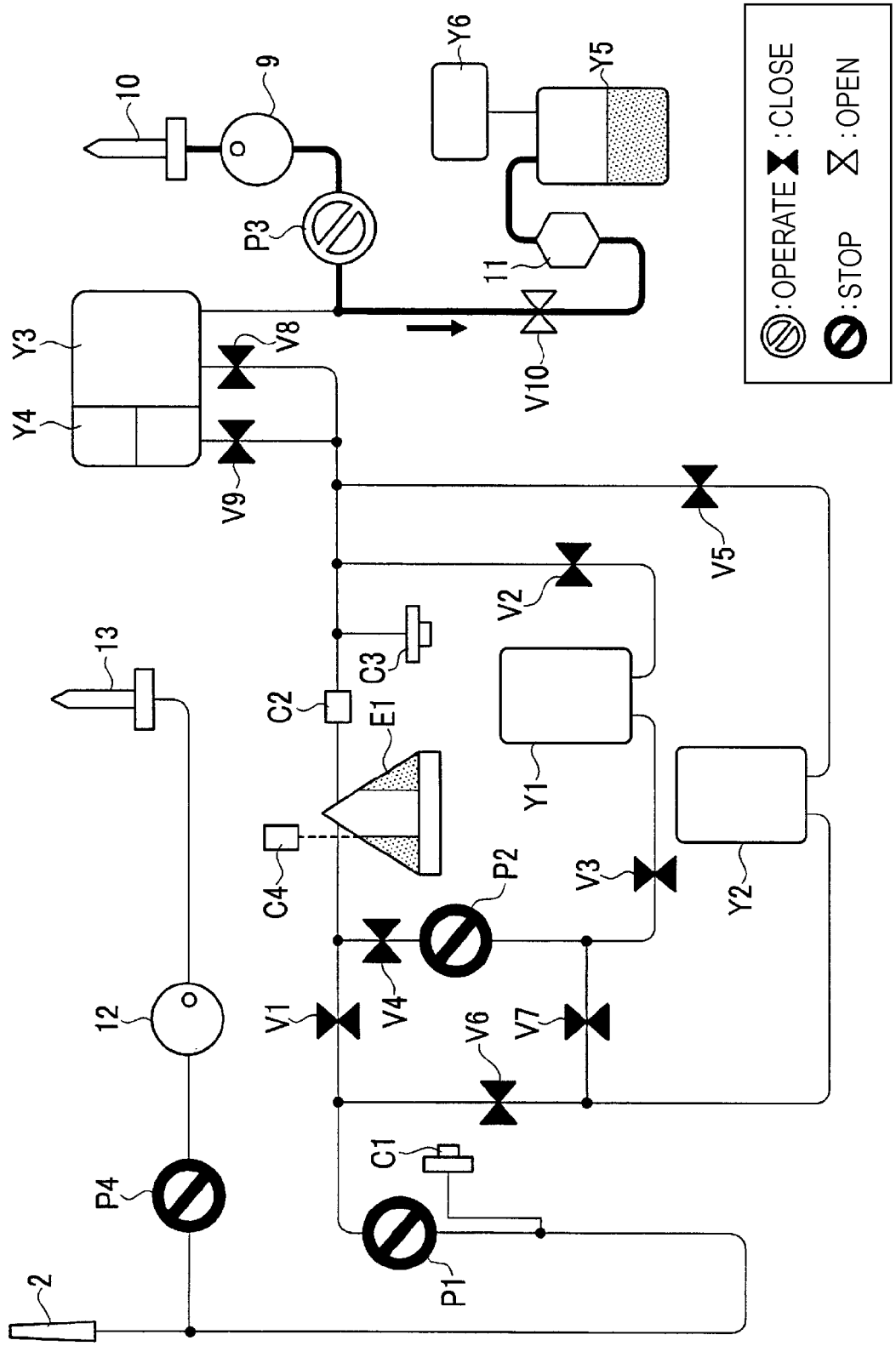
FIG. 14 illustrates a final processing step of platelet liquid.

After confirming that the high-concentration platelet liquid stored in the platelet intermediate bag Y3 has completely been taken out, the third blood pump P3 is operated to inject the platelet reserve liquid remaining in the platelet reserve liquid bottle into the platelet bag Y5, through the bottle needle 10 coupled to the platelet reserve liquid bottle, the sterilizing filter 9, and the white blood cell removal filter 11, as illustrated in FIG. 14. In this manner, already filtered high-concentration platelet liquid remaining on the white blood cell removal filter 11 is recovered. Then, two tubes of the platelet bag are sealed. In this manner, the platelet bag Y5 storing high-concentration platelet liquid is prepared.

According to the working example, as described above in detail, (1) blood component separation device includes a centrifuge bowl E1 for separating a predetermined blood component from blood and a container (plasma bag Y1, platelet intermediate bag Y3) for containing the centrifugally separated predetermined blood component, and performs (a) centrifugal separation step of introducing the whole blood drawn from a blood donor into the centrifuge bowl E1 with a first blood pump P1 to separate the whole blood into a plurality of blood components, (b) critical flow step (circulation flow step of the present invention) of introducing the plasma (the first blood component), among centrifugally separated blood components, stored in the plasma bag Y1 (first container) into the centrifuge bowl E1 together with whole blood, and (c) circulation/acceleration step of introducing, after separating the plasma in the critical flow step, only the plasma stored in the plasma bag Y1 into the centrifuge bowl E1 with the second blood pump P2 to circulate the plasma for a predetermined period of time, and increasing the circulation speed in the centrifuge bowl E1 to separate and collect platelets (the second blood component). The blood component separation device is characterized in that the whole blood drawn from the blood donor is temporarily stored in the temporary storage bag Y2 (temporary storage container) during at least a period of time in the circulation/acceleration step, one of the tubes coupled to the temporary storage bag Y2, which is the tube T11b, is coupled to an outlet port E1b of the centrifuge bowl E1 via the tube T11a, the tube T15, and the tube T5, and the other one of the tubes, which is the tube T12, is coupled, via the tube T13b and the tube T13a, between the plasma bag Y1 and the second blood pump P2. Moreover, (2) blood component separation device according to (1) is preferably characterized in that, in the centrifugal separation step in the following cycle, at least either the whole blood or the low-concentration platelet liquid stored in the temporary storage bag Y2 in the previous cycle is introduced into the centrifuge bowl E1 by the second blood pump P2, so that either of the whole blood or the low-concentration platelet liquid stored in the previous cycle can quickly and surely be introduced into the centrifuge bowl E1.

(3) The blood component separation device according to (1) or (2) is preferably characterized in that the other tube T12 is branched and the one of the branched tube is coupled, via the tube T13b, the tube T13a, and the tube T2, to the outlet port of the first blood pump P1, and the two tubes T13b and T14a branched from the other tube T12 are coupled to the sixth open/close valve V6 and the seventh open/close valve V7, respectively, so that at least either the whole blood or the low-concentration second blood component stored in the temporary storage bag Y2 can be introduced into the centrifugal separator E1 by using the second blood pump P2 without providing any additional blood pump. Thus, the device need not be large in size and the cost can be reduced. Furthermore, compared to a device using a difference in elevation instead of a blood pump, at least either the whole blood or the low-concentration second blood component stored in the temporary storage bag Y2 can be introduced into the centrifugal separator E1 in a short time by using the blood pump.

(4) The blood component separation device according to any one of (1) to (3) performs (d) blood returning step, performed after collecting platelets in the circulation/acceleration step, of returning to the blood donor the blood component that is not collected, and is characterized in that the whole blood stored in the temporary storage bag Y2 (temporary storage container) is introduced, in the centrifugal separation step in the following cycle, into the centrifuge bowl E1 together with the whole blood drawn in the following cycle, where the steps (a) to (d) constitute one cycle. In this manner, the whole blood can be drawn from the blood donor in parallel with the circulation/acceleration step in the first cycle (the present cycle). Thus, the time for drawing whole blood in the second cycle (the following cycle) and therefore the total time for the total process can be reduced, thereby reducing the binding time of the blood donor.

For example, typical time periods in one cycle are about twelve minutes for blood drawing (centrifugal separation step+critical flow step), 30 to 40 seconds for the circulation step in the circulation/acceleration step, 20 to 30 seconds for the acceleration step in the circulation/acceleration step, and about five minutes for the blood returning. According to the present invention, since blood drawing is performed for about one minute in the first cycle, the blood drawing time in the second cycle can be reduced by one minute to about eleven minutes. Similarly, when total of three cycles are performed, the blood drawing time in the third cycle can be reduced by one minute to about eleven minutes.

For a blood donor, the amount of blood circulating outside the body increases, though it may not be a problem for 90% of blood donors. The donor may be checked in advance to see if there is a problem to increase the amount of blood circulating outside the body. If there may be a problem, a switching unit can be used so as not to perform the drawing of whole blood in parallel with the circulation/acceleration step in the first cycle (the present cycle), but to perform the drawing of whole blood in the second cycle (the following cycle) after returning blood. It goes without saying that the drawing of whole blood for the following cycle is not performed in the last cycle, because there is no cycle following the last cycle.

(5) The blood component separation device according to any one of (1) to (4) is preferably characterized in that the circulation/acceleration step includes a first collecting step of transferring a portion of platelet liquid (second blood component) with low-concentration (low-concentration second blood component) to a temporary storage bag Y2 and a second collecting step of collecting a portion of platelet liquid with high-concentration (high-concentration second blood component), and the low-concentration platelet liquid transferred to the temporary storage bag Y2 and the whole blood collected in the temporary storage bag Y2 in the following cycle are introduced into the centrifuge bowl E1 together with the whole blood drawn in a following cycle. Therefore, the device can be used for the BC recycling for obtaining platelets with high-concentration, and since the whole blood can be drawn from the blood donor in parallel with the circulation/acceleration step in the first cycle (the present cycle), the time for drawing whole blood in the second cycle (the following cycle) and therefore the time for the total process can be reduced, thereby reducing the binding time of the blood donor.

(6) The blood component separation device according to (5) preferably includes the second container for temporarily storing the low-concentration platelet liquid in the circulation/acceleration step, and is characterized in that the second container also serves as the temporary storage bag Y2. Therefore, an additional second container is not required so that the device need not be made large in size, and since a special disposable second container is not necessary, the cost can be reduced.

The working examples of the present invention are described above in detail. The present invention is not limited to the aforementioned working examples and can be used for various applications. For example, in the working example, the temporary storage bag Y2 serves as a buffy coat bag as well as a whole blood bag, although the buffy coat bag may individually be provided in parallel with the whole blood bag. In the working example, the drawing of whole blood is performed in parallel throughout the entire period of the circulation/acceleration step, although the drawing of whole blood may be performed in parallel with a certain time period. In the working example, the drawing of whole blood is performed in parallel with the circulation/acceleration step, although the switching unit may be provided to the blood component separation device so as not to draw whole blood in parallel but to draw whole blood in a conventional manner.

REFERENCE SIGNS LIST 14 centrifuge bowl drive unit
E1 centrifuge bowl
Y1 plasma bag (first container)
Y2 temporary storage bag (second container)
Y3 platelet intermediate bag (third container)
Y4, Y6 air bag
Y5 platelet bag
C2 turbidity sensor
C4 interface sensor
P1 first blood pump
P2 second blood pump
P3 third blood pump
P4 ACD pump
PPP plasma (first blood component)
PLT platelet (second blood component)
WBC white blood cell
BC buffy coat
RBC red blood cell

The invention claimed is:

1. A method of controlling a blood component separation device comprising:
a centrifugal separator for separating a predetermined blood component from blood; and
a container for containing the predetermined blood component that is centrifugally separated, wherein the method comprises:
(a) a centrifugal separation step of introducing whole blood drawn from a blood donor into the centrifugal separator with a first blood pump to separate the whole blood into a plurality of blood components,
(b) a circulation flow step of introducing a predetermined first blood component, among centrifugally separated blood components, into a first container together with whole blood, and
(c) a circulation/acceleration step of stopping supply of whole blood to the centrifugal separator after separating a predetermined amount of the first blood component in the circulation flow step, introducing only the first blood component stored in the first container to the centrifugal separator with a second blood pump to circulate the first blood component for a predetermined period of time, and increasing a circulation speed in the centrifugal separator to separate and collect a second blood component,
wherein whole blood drawn from the blood donor is temporarily stored in a temporary storage container during at least a period of time in the circulation/acceleration step, and
a first tube coupled to the temporary storage container is further coupled to an outlet port of the centrifugal separator and a second tube also coupled to the temporary storage container is further coupled between the first container and the second blood pump.

2. The method according to claim 1, wherein the second tube is branched such that a first branch tube is coupled between the first container and the second blood pump and a second branch tube is coupled to an outlet port of the first blood pump,
an open/close valve is provided on each of two branch tubes branched from the second tube,
an open/close valve is provided to an outlet port of the second blood pump, and
an open/close valve is provided to an outlet port of the first container.

3. The method according to claim 2, wherein the blood component separation device is configured to perform
(d) a blood returning step, which is performed after collecting a predetermined amount of the second blood component in the circulation/acceleration step, of returning to the blood donor a blood component that is not collected, and
whole blood stored in the temporary storage container is introduced, in the centrifugal separation step in a following cycle, into the centrifugal separator together with whole blood drawn in the following cycle, the steps (a) to (d) constituting one cycle.

4. The method according to claim 3, wherein,
the circulation/acceleration step includes:
a first collecting step of transferring a portion of the second blood component with low-concentration to the temporary storage container; and
a second collecting step of collecting a portion of the second blood component with high-concentration, and
the second blood component with low-concentration transferred to the temporary storage container and whole blood collected in the temporary storage container in a following cycle are introduced into the centrifugal separator together with whole blood drawn in the following cycle.

5. The method according to claim 2, wherein, the circulation/acceleration step includes:
a first collecting step of transferring a portion of the second blood component with low-concentration to the temporary storage container; and
a second collecting step of collecting a portion of the second blood component with high-concentration, and
the second blood component with low-concentration transferred to the temporary storage container and whole blood collected in the temporary storage container in a following cycle are introduced into the centrifugal separator together with whole blood drawn in the following cycle.

6. The method according to claim 1, wherein the blood component separation device is configured to perform
(d) a blood returning step, which is performed after collecting a predetermined amount of the second blood component in the circulation/acceleration step, of returning to the blood donor a blood component that is not collected, and whole blood stored in the temporary storage container is introduced, in the centrifugal separation step in a following cycle, into the centrifugal separator together with whole blood drawn in the following cycle, the steps (a) to (d) constituting one cycle.

7. The method according to claim 6, wherein, the circulation/acceleration step includes:
   a first collecting step of transferring a portion of the second blood component with low-concentration to the temporary storage container; and
   a second collecting step of collecting a portion of the second blood component with high-concentration, and
   the second blood component with low-concentration transferred to the temporary storage container and whole blood collected in the temporary storage container in a following cycle are introduced into the centrifugal separator together with whole blood drawn in the following cycle.

8. The method according to claim 1, wherein the second blood pump introduces, in the centrifugal separation step in a following cycle, at least either whole blood or a low-concentration second blood component stored in the temporary storage container in a previous cycle into the centrifugal separator.

9. The method according to claim 8, wherein the second tube is branched such that a first branch tube is coupled between the first container and the second blood pump and a second branch tube is coupled to an outlet port of the first blood pump,
   an open/close valve is provided on each of two branched tubes branched from the second tube,
   an open/close valve is provided to an outlet port of the second blood pump, and
   an open/close valve is provided to an outlet port of the first container.

10. The method according to claim 9, wherein the blood component separation device is configured to perform
   (d) a blood returning step, which is performed after collecting a predetermined amount of the second blood component in the circulation/acceleration step, of returning to the blood donor a blood component that is not collected, and
   whole blood stored in the storage container is introduced, in the centrifugal separation step in a following cycle, into the centrifugal separator together with whole blood drawn in the following cycle, the steps (a) to (d) constituting one cycle.

11. The method according to claim 10, wherein, the circulation/acceleration step includes:
   a first collecting step of transferring a portion of the second blood component with low-concentration to the temporary storage container; and
   a second collecting step of collecting a portion of the second blood component with high-concentration, and
   the second blood component with low-concentration transferred to the temporary storage container and whole blood collected in the temporary storage container in a following cycle are introduced into the centrifugal separator together with whole blood drawn in the following cycle.

12. The method according to claim 9, wherein, the circulation/acceleration step includes:
   a first collecting step of transferring a portion of the second blood component with low-concentration to the temporary storage container; and
   a second collecting step of collecting a portion of the second blood component with high-concentration, and
   the second blood component with low-concentration transferred to the temporary storage container and whole blood collected in the temporary storage container in a following cycle are introduced into the centrifugal separator together with whole blood drawn in the following cycle.

13. The method according to claim 8, wherein the blood component separation device is configured to perform
   (d) a blood returning step, which is performed after collecting a predetermined amount of the second blood component in the circulation/acceleration step, of returning to the blood donor a blood component that is not collected, and
   whole blood stored in the storage container is introduced, in the centrifugal separation step in a following cycle, into the centrifugal separator together with whole blood drawn in the following cycle, the steps (a) to (d) constituting one cycle.

14. The method according to claim 13, wherein, the circulation/acceleration step includes:
   a first collecting step of transferring a portion of the second blood component with low-concentration to the temporary storage container; and
   a second collecting step of collecting a portion of the second blood component with high-concentration, and
   the second blood component with low-concentration transferred to the temporary storage container and whole blood collected in the temporary storage container in a following cycle are introduced into the centrifugal separator together with whole blood drawn in the following cycle.

15. The method according to claim 8, wherein, the circulation/acceleration step includes:
   a first collecting step of transferring a portion of the second blood component with low-concentration to the temporary storage container; and
   a second collecting step of collecting a portion of the second blood component with high-concentration, and
   the second blood component with low-concentration transferred to the temporary storage container and whole blood collected in the temporary storage container in a following cycle are introduced into the centrifugal separator together with whole blood drawn in the following cycle.

16. The method according to claim 1, wherein, the circulation/acceleration step includes:
   a first collecting step of transferring a portion of the second blood component with low-concentration to the temporary storage container; and
   a second collecting step of collecting a portion of the second blood component with high-concentration, and
   the second blood component with low-concentration transferred to the temporary storage container and whole blood collected in the temporary storage container in a following cycle are introduced into the centrifugal separator together with whole blood drawn in the following cycle.

* * * * *